US008119109B2

(12) United States Patent
Tamarkin et al.

(10) Patent No.: US 8,119,109 B2
(45) Date of Patent: Feb. 21, 2012

(54) FOAMABLE COMPOSITIONS, KITS AND METHODS FOR HYPERHIDROSIS

(75) Inventors: Dov Tamarkin, Maccabim (IL); Meir Eini, Ness Ziona (IL); Ella Zlatkis, Rehovot (IL)

(73) Assignee: Foamix Ltd., Rehovot (IL)

( * ) Notice: Subject to any disclaimer, the term of this patent is extended or adjusted under 35 U.S.C. 154(b) by 1280 days.

(21) Appl. No.: 11/717,897

(22) Filed: Mar. 13, 2007

(65) Prior Publication Data

US 2007/0253911 A1    Nov. 1, 2007

Related U.S. Application Data

(63) Continuation-in-part of application No. 10/911,367, filed on Aug. 4, 2004, application No. 11/717,897, which is a continuation-in-part of application No. 10/532,618, filed as application No. PCT/IB03/05527 on Oct. 24, 2003, application No. 11/717,897, which is a continuation-in-part of application No. 11/078,902, filed on Mar. 11, 2005.

(60) Provisional application No. 60/492,385, filed on Aug. 4, 2003, provisional application No. 60/429,546, filed on Nov. 29, 2002, provisional application No. 60/781,868, filed on Mar. 13, 2006, provisional application No. 60/897,638, filed on Jan. 26, 2007, provisional application No. 60/899,176, filed on Feb. 2, 2007.

(30) Foreign Application Priority Data

Oct. 25, 2002  (IL) .......................................... 152486

(51) Int. Cl.
*A61K 8/02* (2006.01)
*A61K 8/28* (2006.01)
*A61K 8/26* (2006.01)
*A61K 9/12* (2006.01)
*A61K 33/06* (2006.01)

(52) U.S. Cl. ................ 424/65; 424/66; 424/67; 424/68; 424/401; 424/682

(58) Field of Classification Search ..................... 424/65, 424/66, 67, 68, 401, 682
See application file for complete search history.

(56) References Cited

U.S. PATENT DOCUMENTS

| | | | |
|---|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,968,628 A | 1/1961 | Reed |
| 3,062,715 A | 11/1962 | Reese |
| 3,067,784 A | 12/1962 | Gorman |
| 3,092,255 A | 6/1963 | Hohman |
| 3,141,821 A | 7/1964 | Compeau |
| 3,142,420 A | 7/1964 | Gawthrop |
| 3,144,386 A | 8/1964 | Brighttenback |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienciewicz |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernaadez |
| 3,346,451 A | 10/1967 | Collins et al. |
| 3,366,494 A | 1/1968 | Bower |
| 3,369,034 A | 2/1968 | Chalmers |
| 3,384,541 A | 5/1968 | Clark et al. |
| 3,395,214 A * | 7/1968 | Mummert ....................... 424/47 |
| 3,395,215 A | 7/1968 | Warren |
| 3,401,849 A | 9/1968 | Weber, III |
| 3,419,658 A | 12/1968 | Amsdon |
| 3,527,559 A | 9/1970 | Sliwinski |
| 3,559,890 A | 2/1971 | Brooks et al. |
| 3,561,262 A | 2/1971 | Borocki |
| 3,574,821 A | 4/1971 | Pfirrmann et al. |
| 3,577,518 A | 5/1971 | Shepherd |
| 3,751,562 A | 8/1973 | Nichols |

(Continued)

FOREIGN PATENT DOCUMENTS

AU    198780257    9/1986

(Continued)

OTHER PUBLICATIONS

Gelbard et al., "Primary Pediatric Hyperhidrosis: A Review of Current Treatment Options," Pediatric Dermatology, 2008, 25(6), pp. 591-598.*

(Continued)

*Primary Examiner* — James H. Alstrum-Acevedo
(74) *Attorney, Agent, or Firm* — Wilmer Cutler Pickering Hale and Dorr LLP

(57) ABSTRACT

The composition of the present invention is geared towards treating hyperhidrosis or any condition involving and/or promoting excessive sweating, typically involving the whole body, include hyperthyroidism or similar endocrine disorders; endocrine treatment for prostatic cancer or other types of malignant disorder; severe psychiatric disorders; obesity and menopause. The foamable composition of the present invention is suitable for treating palmar hyperhidrosis; axillary hyperhidrosis; plantar hyperhidrosis; hyperhidrosis of the trunk and/or the thighs; and facial hyperhidrosis; and any combination of them consisting of a therapeutic foamable composition including: an active agent, suitable for the treatment or prevention of hyperhidrosis.

45 Claims, No Drawings

U.S. PATENT DOCUMENTS

| | | |
|---|---|---|
| 3,770,648 A | 11/1973 | Mackes |
| 3,787,566 A | 1/1974 | Gauvreau |
| 3,819,524 A | 6/1974 | Schubert et al. |
| 3,849,580 A | 11/1974 | Sejpal |
| 3,866,800 A | 2/1975 | Schmitt |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,923,970 A | 12/1975 | Breuer |
| 3,929,985 A | 12/1975 | Webb, Jr. |
| 3,959,160 A | 5/1976 | Horsler et al. |
| 3,962,150 A | 6/1976 | Viola |
| 3,963,833 A * | 6/1976 | DeSalva et al. ............... 424/68 |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom et al. |
| 4,001,391 A | 1/1977 | Feinstone et al. |
| 4,001,442 A | 1/1977 | Stahlberger et al. |
| 4,019,657 A | 4/1977 | Spitzer et al. |
| 4,100,426 A | 7/1978 | Baranowski et al. |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,160,827 A | 7/1979 | Cho et al. |
| 4,213,979 A | 7/1980 | Levine |
| 4,214,000 A | 7/1980 | Papa |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,292,250 A | 9/1981 | DeLuca et al. |
| 4,292,326 A | 9/1981 | Nazzaro-Porro et al. |
| 4,299,826 A | 11/1981 | Luedders |
| 4,310,510 A | 1/1982 | Sherman et al. |
| 4,323,694 A | 4/1982 | Scala, Jr. |
| 4,335,120 A | 6/1982 | Holick et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,439,416 A | 3/1984 | Cordon et al. |
| 4,439,441 A | 3/1984 | Hallesy et al. |
| 4,447,486 A | 5/1984 | Hoppe et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,627,973 A | 12/1986 | Moran et al. |
| 4,628,063 A | 12/1986 | Haines et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,741,855 A | 5/1988 | Grote et al. |
| 4,752,465 A | 6/1988 | Mackles |
| 4,770,634 A | 9/1988 | Pellico |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,885,282 A | 12/1989 | Thornfeldt |
| 4,897,262 A | 1/1990 | Nandagiri et al. |
| 4,906,453 A | 3/1990 | Tsoucalas |
| 4,913,893 A | 4/1990 | Varco et al. |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,970,067 A | 11/1990 | Panandiker et al. |
| 4,975,466 A | 12/1990 | Bottcher et al. |
| 4,981,677 A | 1/1991 | Thau |
| 4,981,679 A | 1/1991 | Briggs et al. |
| 4,981,845 A | 1/1991 | Pereira et al. |
| 4,992,478 A | 2/1991 | Geria |
| 5,002,540 A | 3/1991 | Brodman et al. |
| 5,002,680 A | 3/1991 | Schmidt et al. |
| 5,007,556 A | 4/1991 | Lover |
| 5,015,471 A | 5/1991 | Birtwistle et al. |
| 5,019,375 A * | 5/1991 | Tanner et al. ............... 424/66 |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,279,819 A | 1/1994 | Hayes |
| 5,286,475 A | 2/1994 | Louvet et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |

| | | | | | | |
|---|---|---|---|---|---|---|
| 5,385,943 | A | 1/1995 | Nazzaro-Porro | 5,866,040 | A | 2/1999 | Nakama et al. |
| 5,389,676 | A | 2/1995 | Michaels | 5,869,529 | A | 2/1999 | Sintov et al. |
| 5,397,312 | A | 3/1995 | Rademaker et al. | 5,871,720 | A | 2/1999 | Gutierrez et al. |
| 5,411,992 | A | 5/1995 | Eini et al. | 5,877,216 | A | 3/1999 | Place et al. |
| 5,422,361 | A | 6/1995 | Munayyer et al. | 5,879,469 | A | 3/1999 | Avram et al. |
| 5,429,815 | A | 7/1995 | Faryniarz et al. | 5,885,581 | A | 3/1999 | Massand |
| 5,435,996 | A | 7/1995 | Glover et al. | 5,889,028 | A | 3/1999 | Sandborn et al. |
| 5,447,725 | A | 9/1995 | Damani et al. | 5,889,054 | A | 3/1999 | Yu et al. |
| 5,449,520 | A | 9/1995 | Frigerio et al. | 5,891,458 | A | 4/1999 | Britton et al. |
| 5,451,404 | A | 9/1995 | Furman | 5,902,574 | A | 5/1999 | Stoner et al. |
| 5,482,965 | A | 1/1996 | Rajadhyaksha | 5,902,789 | A | 5/1999 | Stoltz |
| 5,491,245 | A | 2/1996 | Gruning et al. | 5,905,092 | A | 5/1999 | Osborne et al. |
| 5,500,211 | A | 3/1996 | George et al. | 5,911,981 | A | 6/1999 | Dahms et al. |
| 5,508,033 | A | 4/1996 | Briand et al. | 5,912,007 | A | 6/1999 | Pan et al. |
| 5,512,555 | A | 4/1996 | Waldstreicher | 5,914,122 | A | 6/1999 | Otterbeck et al. |
| 5,514,367 | A | 5/1996 | Lentini et al. | 5,914,310 | A | 6/1999 | Li et al. |
| 5,514,369 | A | 5/1996 | Salka et al. | 5,922,331 | A | 7/1999 | Mausner |
| 5,520,918 | A | 5/1996 | Smith | 5,948,682 | A | 9/1999 | Moloney |
| 5,523,078 | A | 6/1996 | Baylin | 5,951,993 | A | 9/1999 | Scholz et al. |
| 5,527,534 | A | 6/1996 | Myhling | 5,952,373 | A | 9/1999 | Lanzendorfer et al. |
| 5,527,822 | A | 6/1996 | Scheiner | 5,952,392 | A | 9/1999 | Katz et al. |
| 5,529,770 | A | 6/1996 | McKinzie et al. | 5,961,957 | A | 10/1999 | McAnalley |
| 5,531,703 | A | 7/1996 | Skwarek et al. | 5,972,310 | A | 10/1999 | Sachetto |
| 5,534,261 | A | 7/1996 | Rodgers et al. | 5,976,555 | A | 11/1999 | Liu et al. |
| 5,536,743 | A | 7/1996 | Borgman | 5,980,904 | A | 11/1999 | Leverett et al. |
| 5,540,853 | A | 7/1996 | Trinh et al. | 5,993,846 | A | 11/1999 | Friedman et al. |
| 5,545,401 | A | 8/1996 | Shanbrom | 6,006,948 | A | 12/1999 | Auer |
| 5,567,420 | A | 10/1996 | McEleney et al. | 6,019,967 | A | 2/2000 | Breton et al. |
| 5,576,016 | A | 11/1996 | Amselem et al. | 6,024,942 | A | 2/2000 | Tanner et al. |
| 5,578,315 | A | 11/1996 | Chien et al. | 6,030,630 | A | 2/2000 | Fleury et al. |
| 5,585,104 | A | 12/1996 | Ha et al. | 6,033,647 | A | 3/2000 | Touzan et al. |
| 5,589,157 | A | 12/1996 | Hatfield | 6,039,936 | A | 3/2000 | Restle et al. |
| 5,589,515 | A | 12/1996 | Suzuki et al. | 6,042,848 | A | 3/2000 | Lawyer et al. |
| 5,603,940 | A | 2/1997 | Candau et al. | 6,045,779 | A | 4/2000 | Mueller et al. |
| 5,605,679 | A | 2/1997 | Hansenne et al. | 6,071,536 | A | 6/2000 | Suzuki et al. |
| 5,611,463 | A | 3/1997 | Favre | 6,075,056 | A | 6/2000 | Quigley, Jr. et al. |
| 5,612,056 | A | 3/1997 | Jenner et al. | 6,080,394 | A | 6/2000 | Lin et al. |
| 5,614,171 | A | 3/1997 | Clavenna et al. | 6,087,317 | A | 7/2000 | Gee |
| 5,635,469 | A | 6/1997 | Fowler et al. | 6,090,772 | A | 7/2000 | Kaiser et al. |
| 5,641,480 | A | 6/1997 | Vermeer | 6,093,408 | A | 7/2000 | Hasenoehrl et al. |
| 5,643,600 | A | 7/1997 | Mathur | 6,110,477 | A | 8/2000 | Hernandez et al. |
| 5,645,842 | A | 7/1997 | Gruning et al. | 6,113,888 | A | 9/2000 | Castro et al. |
| 5,650,554 | A | 7/1997 | Moloney | 6,116,466 | A | 9/2000 | Gueret et al. |
| 5,658,749 | A | 8/1997 | Thornton | 6,121,210 | A | 9/2000 | Taylor |
| 5,658,956 | A | 8/1997 | Martin et al. | 6,126,920 | A | 10/2000 | Jones et al. |
| 5,663,208 | A | 9/1997 | Martin | 6,140,355 | A | 10/2000 | Egidio et al. |
| 5,672,634 | A | 9/1997 | Tseng et al. | 6,146,645 | A | 11/2000 | Deckers et al. |
| 5,679,324 | A | 10/1997 | Lisboa et al. | 6,146,664 | A | 11/2000 | Siddiqui |
| 5,683,710 | A | 11/1997 | Akemi et al. | 6,162,834 | A | 12/2000 | Sebillotte-Arnaud et al. |
| 5,695,551 | A | 12/1997 | Buckingham et al. | 6,165,455 | A | 12/2000 | Torgerson et al. |
| 5,700,396 | A | 12/1997 | Suzuki et al. | 6,168,576 | B1 | 1/2001 | Reynolds |
| 5,716,611 | A | 2/1998 | Oshlack et al. | 6,171,347 | B1 | 1/2001 | Kunz et al. |
| 5,719,122 | A | 2/1998 | Chiodini et al. | 6,180,669 | B1 | 1/2001 | Tamarkin |
| 5,719,197 | A | 2/1998 | Kanios et al. | 6,183,762 | B1 | 2/2001 | Deckers et al. |
| 5,725,872 | A | 3/1998 | Stamm et al. | 6,186,367 | B1 | 2/2001 | Harrold |
| 5,730,964 | A | 3/1998 | Waldstreicher | 6,187,290 | B1 | 2/2001 | Gilchrist et al. |
| 5,733,558 | A | 3/1998 | Breton et al. | 6,189,810 | B1 | 2/2001 | Nerushai et al. |
| 5,733,572 | A | 3/1998 | Unger et al. | 6,204,285 | B1 | 3/2001 | Fabiano et al. |
| 5,747,049 | A | 5/1998 | Tominaga | 6,210,656 | B1 | 4/2001 | Touzan et al. |
| 5,753,241 | A | 5/1998 | Ribier et al. | 6,210,742 | B1 | 4/2001 | Deckers et al. |
| 5,753,245 | A | 5/1998 | Fowler et al. | 6,214,318 | B1 | 4/2001 | Osipow et al. |
| 5,759,520 | A | 6/1998 | Sachetto | 6,221,381 | B1 | 4/2001 | Shelford et al. |
| 5,759,579 | A | 6/1998 | Singh et al. | 6,224,888 | B1 | 5/2001 | Vatter et al. |
| 5,767,104 | A | 6/1998 | Bar-Shalom et al. | 6,231,837 | B1 | 5/2001 | Stroud et al. |
| 5,783,202 | A | 7/1998 | Tomlinson et al. | 6,232,315 | B1 | 5/2001 | Shafer et al. |
| 5,792,448 | A | 8/1998 | Dubief et al. | 6,251,369 | B1 | 6/2001 | Stoltz |
| 5,792,922 | A | 8/1998 | Moloney et al. | 6,258,374 | B1 | 7/2001 | Friess et al. |
| 5,804,546 | A | 9/1998 | Hall et al. | 6,271,295 | B1 | 8/2001 | Powell et al. |
| 5,817,322 | A | 10/1998 | Xu et al. | 6,274,150 | B1 | 8/2001 | Simonnet et al. |
| 5,824,650 | A | 10/1998 | De Lacharriere et al. | 6,287,546 | B1 | 9/2001 | Reich et al. |
| 5,833,960 | A | 11/1998 | Gers-Barlag et al. | 6,294,550 | B1 | 9/2001 | Place et al. |
| 5,837,270 | A | 11/1998 | Burgess | 6,299,023 | B1 | 10/2001 | Arnone |
| 5,840,744 | A | 11/1998 | Borgman | 6,299,900 | B1 | 10/2001 | Reed et al. |
| 5,840,771 | A | 11/1998 | Oldham et al. | 6,305,578 | B1 | 10/2001 | Hildebrandt et al. |
| 5,843,411 | A | 12/1998 | Hernandez et al. | 6,306,841 | B1 | 10/2001 | Place et al. |
| 5,846,983 | A | 12/1998 | Sandborn et al. | 6,308,863 | B1 | 10/2001 | Harman |
| 5,849,042 | A | 12/1998 | Lim et al. | 6,319,913 | B1 | 11/2001 | Mak et al. |
| 5,856,452 | A | 1/1999 | Moloney et al. | 6,328,950 | B1 | 12/2001 | Franzke et al. |
| 5,858,371 | A | 1/1999 | Singh et al. | 6,333,362 | B1 | 12/2001 | Lorant |

| | | | | | |
|---|---|---|---|---|---|
| 6,335,022 B1 | 1/2002 | Simonnet et al. | 7,235,251 B2 | 6/2007 | Hamer et al. |
| 6,341,717 B2 | 1/2002 | Auer | 7,270,828 B2 | 9/2007 | Masuda et al. |
| 6,344,218 B1 | 2/2002 | Dodd et al. | 7,654,415 B2 | 2/2010 | van der Heijden |
| 6,358,541 B1 | 3/2002 | Goodman | 7,682,623 B2 | 3/2010 | Eini et al. |
| 6,372,234 B1 | 4/2002 | Deckers et al. | 7,700,076 B2 | 4/2010 | Tamarkin et al. |
| 6,375,960 B1 | 4/2002 | Simonnet et al. | 2001/0006654 A1 | 7/2001 | Cannell et al. |
| 6,383,471 B1 | 5/2002 | Chen et al. | 2001/0027218 A1 | 10/2001 | Stern et al. |
| 6,395,258 B1 | 5/2002 | Steer | 2001/0036450 A1 | 11/2001 | Verite et al. |
| 6,395,300 B1 | 5/2002 | Straub et al. | 2002/0002151 A1 | 1/2002 | Ono et al. |
| 6,403,061 B1 | 6/2002 | Candau et al. | 2002/0004063 A1 | 1/2002 | Zhang |
| 6,403,069 B1 | 6/2002 | Chopra et al. | 2002/0013481 A1 | 1/2002 | Schonrock et al. |
| 6,410,036 B1 | 6/2002 | De Rosa et al. | 2002/0015721 A1 | 2/2002 | Simonnet et al. |
| 6,423,323 B2 | 7/2002 | Neubourg | 2002/0032171 A1 | 3/2002 | Chen et al. |
| 6,428,772 B1 | 8/2002 | Singh et al. | 2002/0035046 A1 | 3/2002 | Lukenbach et al. |
| 6,433,003 B1 * | 8/2002 | Bobrove et al. ............... 514/424 | 2002/0035087 A1 | 3/2002 | Barclay |
| 6,433,024 B1 | 8/2002 | Popp et al. | 2002/0035182 A1 | 3/2002 | L'Alloret et al. |
| 6,433,033 B1 | 8/2002 | Isobe et al. | 2002/0039591 A1 | 4/2002 | Dahle |
| 6,437,006 B1 | 8/2002 | Yoon et al. | 2002/0044659 A1 | 4/2002 | Ohta |
| 6,440,429 B1 | 8/2002 | Torizuka et al. | 2002/0045659 A1 | 4/2002 | Michelet et al. |
| 6,455,076 B1 | 9/2002 | Hahn et al. | 2002/0048798 A1 | 4/2002 | Avery et al. |
| 6,468,989 B1 | 10/2002 | Chang et al. | 2002/0058010 A1 | 5/2002 | Picard-Lesboueyries et al. |
| 6,479,058 B1 | 11/2002 | McCadden | 2002/0072544 A1 | 6/2002 | Miller et al. |
| 6,486,168 B1 | 11/2002 | Skwierczynski et al. | 2002/0098215 A1 | 7/2002 | Douin et al. |
| 6,488,947 B1 | 12/2002 | Bekele | 2002/0111281 A1 | 8/2002 | Vishnupad |
| 6,511,655 B1 | 1/2003 | Muller et al. | 2002/0117516 A1 | 8/2002 | Lasserre et al. |
| 6,514,487 B1 | 2/2003 | Barr | 2002/0134376 A1 | 9/2002 | Castro et al. |
| 6,524,594 B1 | 2/2003 | Santora et al. | 2002/0143188 A1 | 10/2002 | Garvey et al. |
| 6,531,118 B1 | 3/2003 | Gonzalez et al. | 2002/0165170 A1 | 11/2002 | Wilson et al. |
| 6,536,629 B2 | 3/2003 | van der Heijden | 2002/0182162 A1 | 12/2002 | Shahinpoor et al. |
| 6,544,530 B1 | 4/2003 | Friedman | 2002/0187181 A1 | 12/2002 | Godbey et al. |
| 6,548,074 B1 | 4/2003 | Mohammadi | 2002/0198136 A1 | 12/2002 | Mak et al. |
| 6,562,355 B1 | 5/2003 | Renault | 2003/0006193 A1 | 1/2003 | Ikeda et al. |
| 6,566,350 B2 | 5/2003 | Ono et al. | 2003/0031693 A1 | 2/2003 | Breton et al. |
| 6,582,679 B2 | 6/2003 | Stein et al. | 2003/0053961 A1 | 3/2003 | Eccard |
| 6,582,710 B2 | 6/2003 | Deckers et al. | 2003/0078172 A1 | 4/2003 | Guiramand et al. |
| 6,589,509 B2 | 7/2003 | Keller et al. | 2003/0114520 A1 | 6/2003 | Pereira et al. |
| 6,596,287 B2 | 7/2003 | Deckers et al. | 2003/0175232 A1 | 9/2003 | Elliott et al. |
| 6,599,513 B2 | 7/2003 | Deckers et al. | 2003/0175315 A1 | 9/2003 | Yoo et al. |
| 6,620,773 B1 | 9/2003 | Stork et al. | 2003/0180347 A1 | 9/2003 | Young et al. |
| 6,638,981 B2 | 10/2003 | Williams et al. | 2003/0185839 A1 | 10/2003 | Podolsky |
| 6,649,571 B1 | 11/2003 | Morgan | 2003/0206955 A1 | 11/2003 | Sonneville-Aubrun et al. |
| 6,649,574 B2 | 11/2003 | Cardis et al. | 2003/0215472 A1 | 11/2003 | Bonda et al. |
| 6,672,483 B1 | 1/2004 | Roy | 2004/0018228 A1 | 1/2004 | Fischell et al. |
| 6,682,726 B1 | 1/2004 | Marchesi et al. | 2004/0028752 A1 | 2/2004 | Kamm et al. |
| 6,691,898 B2 | 2/2004 | Hurray et al. | 2004/0038912 A1 | 2/2004 | Michelet et al. |
| 6,709,663 B2 | 3/2004 | Espinoza | 2004/0053797 A1 | 3/2004 | Chen et al. |
| 6,723,309 B1 | 4/2004 | Deane | 2004/0058878 A1 | 3/2004 | Walker |
| 6,730,288 B1 | 5/2004 | Abram | 2004/0063787 A1 | 4/2004 | Villanueva |
| 6,753,000 B2 | 6/2004 | Breton et al. | 2004/0078896 A1 | 4/2004 | Hellyer et al. |
| 6,753,167 B2 | 6/2004 | Moloney et al. | 2004/0105825 A1 | 6/2004 | Henning |
| 6,762,158 B2 | 7/2004 | Lukenbach et al. | 2004/0120917 A1 | 6/2004 | Perrier et al. |
| 6,765,001 B2 | 7/2004 | Gans et al. | 2004/0127554 A1 | 7/2004 | Ghisalberti |
| 6,774,114 B2 | 8/2004 | Castiel et al. | 2004/0138179 A1 | 7/2004 | Goldstein et al. |
| 6,777,591 B1 | 8/2004 | Chaudhary | 2004/0151671 A1 | 8/2004 | Abram et al. |
| 6,790,435 B1 | 9/2004 | Ma et al. | 2004/0184992 A1 | 9/2004 | Abram |
| 6,796,973 B1 | 9/2004 | Contente et al. | 2004/0185123 A1 | 9/2004 | Mazzio et al. |
| RE38,623 E | 10/2004 | Hernandez et al. | 2004/0191109 A1 | 9/2004 | Tamarkin |
| 6,811,767 B1 | 11/2004 | Bosch et al. | 2004/0192754 A1 | 9/2004 | Shapira et al. |
| 6,834,778 B2 | 12/2004 | Jinbo et al. | 2004/0197276 A1 | 10/2004 | Takase et al. |
| 6,843,390 B1 | 1/2005 | Bristor | 2004/0197295 A1 | 10/2004 | Riedel et al. |
| 6,875,438 B2 | 4/2005 | Kraemer et al. | 2004/0219122 A1 | 11/2004 | Masuda et al. |
| 6,890,567 B2 | 5/2005 | Nakatsu et al. | 2004/0219176 A1 | 11/2004 | Dominguez |
| 6,902,737 B2 | 6/2005 | Quemin et al. | 2004/0229813 A1 | 11/2004 | DiPiano et al. |
| 6,911,211 B2 | 6/2005 | Eini et al. | 2004/0234475 A1 | 11/2004 | Lannibois-Drean et al. |
| 6,946,120 B2 | 9/2005 | So et al. | 2004/0241099 A1 | 12/2004 | Popp et al. |
| 6,946,139 B2 | 9/2005 | Henning | 2004/0247531 A1 | 12/2004 | Riedel et al. |
| 6,951,654 B2 | 10/2005 | Malcolm et al. | 2004/0253275 A1 | 12/2004 | Eini et al. |
| 6,955,816 B2 | 10/2005 | Klysz | 2004/0258627 A1 | 12/2004 | Riedel et al. |
| 6,956,062 B2 | 10/2005 | Beilfuss et al. | 2004/0265240 A1 | 12/2004 | Tamarkin et al. |
| 6,958,154 B2 | 10/2005 | Andolino Brandt et al. | 2005/0002976 A1 | 1/2005 | Wu |
| 6,967,023 B1 | 11/2005 | Eini et al. | 2005/0013853 A1 | 1/2005 | Gil-Ad et al. |
| 6,969,521 B1 | 11/2005 | Gonzalez et al. | 2005/0031547 A1 | 2/2005 | Tamarkin et al. |
| 6,994,863 B2 | 2/2006 | Eini et al. | 2005/0042182 A1 | 2/2005 | Arkin |
| 7,014,844 B2 | 3/2006 | Mahalingam et al. | 2005/0054991 A1 | 3/2005 | Tobyn et al. |
| 7,029,659 B2 | 4/2006 | Abram et al. | 2005/0069566 A1 | 3/2005 | Tamarkin et al. |
| 7,060,253 B1 | 6/2006 | Mundschenk | 2005/0074414 A1 | 4/2005 | Tamarkin et al. |
| 7,078,058 B2 | 7/2006 | Jones et al. | 2005/0075407 A1 | 4/2005 | Tamarkin et al. |
| 7,137,536 B2 | 11/2006 | Walters et al. | 2005/0079139 A1 | 4/2005 | Jacques et al. |
| 7,225,518 B2 | 6/2007 | Eidenschink et al. | 2005/0084551 A1 | 4/2005 | Jensen et al. |

| | | |
|---|---|---|
| 2005/0101936 A1 | 5/2005 | Gonzales et al. |
| 2005/0106197 A1 | 5/2005 | Blin et al. |
| 2005/0123496 A1 | 6/2005 | Shah et al. |
| 2005/0186142 A1 | 8/2005 | Tamarkin et al. |
| 2005/0186147 A1 | 8/2005 | Tamarkin et al. |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0255048 A1 | 11/2005 | Hirsh et al. |
| 2005/0266035 A1 | 12/2005 | Healy et al. |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0014990 A1 | 1/2006 | Kuechler et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0057168 A1 | 3/2006 | Larm |
| 2006/0088561 A1 | 4/2006 | Eini et al. |
| 2006/0110418 A1 | 5/2006 | Johnson |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0020213 A1 | 1/2007 | Tamarkin |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0175799 A1 | 7/2009 | Tamarkin et al. |
| 2009/0180970 A1 | 7/2009 | Tamarkin et al. |
| 2009/0317338 A1 | 12/2009 | Tamarkin et al. |
| 2010/0221194 A1 | 9/2010 | Loupenok |
| 2011/0002969 A1 | 1/2011 | Serraima et al. |

FOREIGN PATENT DOCUMENTS

| | | |
|---|---|---|
| DE | 1926796 | 11/1965 |
| DE | 4140474 | 6/1993 |
| DE | 10138495 | 2/2003 |
| DE | 102004016710 | 10/2005 |
| EP | 0156507 A1 | 10/1985 |
| EP | 0186453 | 7/1986 |
| EP | 211550 | 2/1987 |
| EP | 0214865 A2 | 3/1987 |
| EP | 0216856 | 4/1987 |
| EP | 0270316 | 6/1988 |
| EP | 297436 | 1/1989 |
| EP | 326196 | 8/1989 |
| EP | 336812 | 10/1989 |
| EP | 0391124 B1 | 10/1990 |
| EP | 0404376 | 12/1990 |
| EP | 414920 | 3/1991 |
| EP | 0484530 A1 | 5/1992 |
| EP | 485299 | 5/1992 |
| EP | 0488089 A1 | 6/1992 |
| EP | 504301 | 9/1992 |
| EP | 0535327 A1 | 4/1993 |
| EP | 0569773 A2 | 11/1993 |
| EP | 0598412 A2 | 5/1994 |
| EP | 0676198 | 10/1995 |
| EP | 0738516 | 10/1996 |
| EP | 0824911 | 2/1998 |
| EP | 829259 | 3/1998 |
| EP | 928608 | 7/1999 |
| EP | 0979654 A1 | 2/2000 |
| EP | 0993827 A1 | 4/2000 |
| EP | 1025836 A1 | 8/2000 |
| EP | 1055425 A2 | 11/2000 |
| EP | 1215258 | 6/2002 |
| EP | 1287813 | 3/2003 |
| EP | 1308169 | 5/2003 |
| EP | 1428521 | 6/2004 |
| EP | 1438946 | 7/2004 |
| EP | 1189579 | 9/2004 |
| EP | 1475381 | 11/2004 |
| EP | 1483001 | 12/2004 |
| EP | 1500385 | 1/2005 |
| EP | 1600185 | 11/2005 |
| EP | 1734927 | 12/2006 |
| EP | 1758547 | 3/2007 |
| EP | 1584324 | 11/2007 |
| EP | 1889609 | 2/2008 |
| FR | 2736824 | 1/1997 |

| | | | | | | |
|---|---|---|---|---|---|---|
| FR | 2774595 A | 8/1999 | | WO | WO-9205142 A1 | 4/1992 |
| FR | 2915891 | 11/2008 | | WO | WO-92/11839 | 7/1992 |
| GB | 808104 | 1/1959 | | WO | WO-9325189 | 12/1993 |
| GB | 808105 | 1/1959 | | WO | WO-9406440 | 3/1994 |
| GB | 922930 | 4/1963 | | WO | WO-96/03115 | 2/1996 |
| GB | 933486 | 8/1963 | | WO | WO-96/19921 | 7/1996 |
| GB | 1026831 | 4/1966 | | WO | WO-9624325 A1 | 8/1996 |
| GB | 1033299 | 6/1966 | | WO | WO-96/27376 | 9/1996 |
| GB | 1081949 A | 9/1967 | | WO | WO-96/39119 | 12/1996 |
| GB | 1121358 | 7/1968 | | WO | WO-9703638 | 2/1997 |
| GB | 1170152 A | 11/1969 | | WO | WO-97/39745 | 10/1997 |
| GB | 1347950 | 2/1974 | | WO | WO-9817282 | 4/1998 |
| GB | 1376649 | 12/1974 | | WO | WO-98/18472 | 5/1998 |
| GB | 1397285 | 6/1975 | | WO | WO-98/19654 | 5/1998 |
| GB | 1408036 | 10/1975 | | WO | WO-98/21955 | 5/1998 |
| GB | 1489672 A | 10/1977 | | WO | WO-98/23291 | 6/1998 |
| GB | 2004746 A | 4/1979 | | WO | WO-98/36733 | 8/1998 |
| GB | 1561423 | 2/1980 | | WO | WO-99/08649 | 2/1999 |
| GB | 2114580 | 8/1983 | | WO | WO-99/20250 | 4/1999 |
| GB | 2153686 | 8/1985 | | WO | WO-99/37282 | 7/1999 |
| GB | 2172298 | 9/1986 | | WO | WO-9953923 | 10/1999 |
| GB | 2166651 | 5/1996 | | WO | WO-00/09082 | 2/2000 |
| GB | 2337461 | 11/1999 | | WO | WO-00/15193 | 3/2000 |
| GB | 2406791 | 4/2005 | | WO | WO-0023051 | 4/2000 |
| IL | 0152486 | 5/2003 | | WO | WO-0033825 | 6/2000 |
| JP | 60001113 | 4/1978 | | WO | WO-0038731 | 7/2000 |
| JP | 55069682 | 5/1980 | | WO | WO-00/61076 | 10/2000 |
| JP | 63119420 | 5/1988 | | WO | WO-00/76461 | 12/2000 |
| JP | 01100111 | 4/1989 | | WO | WO-01/08681 | 2/2001 |
| JP | 01156906 | 6/1989 | | WO | WO-0110961 A1 | 2/2001 |
| JP | 2184614 | 7/1990 | | WO | WO-01/54679 | 8/2001 |
| JP | 02184614 A | 7/1990 | | WO | WO-0162209 A2 | 8/2001 |
| JP | 2255890 | 10/1990 | | WO | WO-01/70242 A2 | 9/2001 |
| JP | 04282311 | 10/1992 | | WO | WO-01/82880 | 11/2001 |
| JP | 4312521 | 11/1992 | | WO | WO-0185102 A2 | 11/2001 |
| JP | 5070340 | 3/1993 | | WO | WO-0185128 | 11/2001 |
| JP | 5213734 | 8/1993 | | WO | WO-0195728 A1 | 12/2001 |
| JP | 6100414 | 4/1994 | | WO | WO-02/00820 | 1/2002 |
| JP | 6329532 | 11/1994 | | WO | WO-0215873 | 2/2002 |
| JP | 7215835 | 8/1995 | | WO | WO-02/28435 | 4/2002 |
| JP | 2008040899 | 2/1996 | | WO | WO-02/41847 A1 | 5/2002 |
| JP | 8119831 | 5/1996 | | WO | WO-02/43490 | 6/2002 |
| JP | 8165218 | 6/1996 | | WO | WO-02/062324 | 8/2002 |
| JP | 8277209 | 10/1996 | | WO | WO-02078667 A1 | 10/2002 |
| JP | 9099553 | 4/1997 | | WO | WO-02/087519 | 11/2002 |
| JP | 9110636 | 4/1997 | | WO | WO-03/000223 A1 | 1/2003 |
| JP | 10114619 | 5/1998 | | WO | WO-03/051294 | 6/2003 |
| JP | 3050289 | 9/1998 | | WO | WO-03/055445 | 7/2003 |
| JP | 11250543 | 9/1999 | | WO | WO-03053292 A1 | 7/2003 |
| JP | 2000017174 A | 1/2000 | | WO | WO-03055454 | 7/2003 |
| JP | 2000080017 | 3/2000 | | WO | WO-03/075851 | 9/2003 |
| JP | 2000128734 | 5/2000 | | WO | WO-03/092641 | 11/2003 |
| JP | 2000191429 | 7/2000 | | WO | WO-2004017962 | 3/2004 |
| JP | 2000239140 | 9/2000 | | WO | WO-2004/037225 | 5/2004 |
| JP | 2000351726 | 12/2000 | | WO | WO-2004037197 | 5/2004 |
| JP | 2000354623 | 12/2000 | | WO | WO-2004/064833 | 8/2004 |
| JP | 2001002526 | 1/2001 | | WO | WO-2004/071479 A1 | 8/2004 |
| JP | 2001019606 | 1/2001 | | WO | WO-2004064769 | 8/2004 |
| JP | 2001072963 | 3/2001 | | WO | WO-2004/078896 | 9/2004 |
| JP | 2002012513 | 1/2002 | | WO | WO-2004078158 | 9/2004 |
| JP | 2002047136 | 2/2002 | | WO | WO-2004093895 | 11/2004 |
| JP | 2002302419 | 10/2002 | | WO | WO-2004112780 A1 | 12/2004 |
| JP | 2003055146 | 2/2003 | | WO | WO-2005/011567 A2 | 2/2005 |
| JP | 2004250435 | 9/2004 | | WO | WO-2005/018530 | 3/2005 |
| JP | 2005314323 | 11/2005 | | WO | WO-2005/018530 A2 | 3/2005 |
| JP | 2005350378 | 12/2005 | | WO | WO-2005/032522 | 4/2005 |
| JP | 2006008574 | 1/2006 | | WO | WO-2005/044219 | 5/2005 |
| JP | 2007131539 | 5/2007 | | WO | WO-2005063224 | 7/2005 |
| KR | 2001003063 | 1/2001 | | WO | WO-2005065652 A1 | 7/2005 |
| UA | 66796 | 6/2004 | | WO | WO-2005/076697 | 8/2005 |
| WO | WO-8201821 | 6/1982 | | WO | WO-2005/097068 | 10/2005 |
| WO | WO-86/05389 | 9/1986 | | WO | WO-2005102282 | 11/2005 |
| WO | WO-88/01863 | 3/1988 | | WO | WO-2005102539 A1 | 11/2005 |
| WO | WO-8801502 | 3/1988 | | WO | WO-2005/117813 | 12/2005 |
| WO | WO-88/08316 | 11/1988 | | WO | WO-2006/003481 A2 | 1/2006 |
| WO | WO-89/06537 | 7/1989 | | WO | WO-2006/010589 | 2/2006 |
| WO | WO-90/05774 | 5/1990 | | WO | WO-2006011046 | 2/2006 |
| WO | WO-91/11991 | 8/1991 | | WO | WO-2006020682 A1 | 2/2006 |
| WO | WO-92/00077 | 1/1992 | | WO | WO-2006/031271 | 3/2006 |

| | | |
|---|---|---|
| WO | WO-2006028339 A1 | 3/2006 |
| WO | WO-2006045170 A2 | 5/2006 |
| WO | WO-2006/091229 | 8/2006 |
| WO | WO-2006079632 A1 | 8/2006 |
| WO | WO-2006081327 | 8/2006 |
| WO | WO-2006/100485 | 9/2006 |
| WO | WO-2006/120682 | 11/2006 |
| WO | WO-2006121610 A2 | 11/2006 |
| WO | WO-2006122158 | 11/2006 |
| WO | WO-2006/129161 | 12/2006 |
| WO | WO-2006131784 A1 | 12/2006 |
| WO | WO-2007/007208 | 1/2007 |
| WO | WO-2007/012977 | 2/2007 |
| WO | WO-2007/023396 | 3/2007 |
| WO | WO-2007031621 A2 | 3/2007 |
| WO | WO-2007/039825 | 4/2007 |
| WO | WO-2007/050543 | 5/2007 |
| WO | WO-2007/054818 | 5/2007 |
| WO | WO-20070/72216 | 6/2007 |
| WO | WO-2007/085899 | 8/2007 |
| WO | WO-2007/085902 | 8/2007 |
| WO | WO-2007/099396 | 9/2007 |
| WO | WO-2007111962 A2 | 10/2007 |
| WO | WO-2008/008397 | 1/2008 |
| WO | WO-2008010963 | 1/2008 |
| WO | WO-2008/038147 | 4/2008 |
| WO | WO-2008/075207 | 6/2008 |
| WO | WO-2008/087148 | 7/2008 |
| WO | WO-2008110872 A2 | 9/2008 |
| WO | WO-2009007785 A2 | 1/2009 |
| WO | WO-2009069006 A2 | 6/2009 |
| WO | WO-2009072007 A2 | 6/2009 |
| WO | WO-2009087578 A2 | 7/2009 |
| WO | WO-2009090495 A2 | 7/2009 |
| WO | WO-2009090558 A2 | 7/2009 |
| WO | WO-2009098595 A2 | 8/2009 |
| WO | WO-2011039637 | 4/2011 |
| WO | WO-2011039638 | 4/2011 |

OTHER PUBLICATIONS

Merck Manual Home Edition article entitled, "Excessive Sweating: Sweating Disorders" accessed on Apr. 14, 2011 at www.merckmanuals.com/home/print/sec18/ch206/ch206c.html.*
Draelos, Z. D., "Antiperspirants and the hyperhidrosis patients," Dermatologic Therapy, 2001, 14, pp. 220-224.*
Alcohol SDA 40B www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, www.arisankimya.com/kozmetik.htm Accessed Dec. 10, 2008.
Barry, B.W. et al, Comparative bio-availability and activity of proprietary topical corticosteroid preparations: vasoconstrictor assays on thirty-one ointments, British Journal of Dermatology, 93, 563-571, 1975.
Benet, et al., Application of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Denatonium Benzoate www.newdruginfo.com/pharmaceopeia/usp28/v28230/usp28nf23s0_m22790.htm Accessed Dec. 9, 2008.

Emulsifiers with HLB values. www.theherbarie.com/files/resources-center/formulating/Emulsifiers_HLB_Values.pdf accessed Aug. 5, 2009 (3 pps).
Ethanol, Accessed //www.sigmaaldrich.com/catalog/ProductDetail.do?N4=E7023SIAL&N5=SEARCH_CONCAT_PNOBRAND_KEY&F=SPEC Dec. 9, 2008, 2 pages.
European Patent Application No. 06831721, Official Action, Feb. 3, 2009, 9 pages.
Flick, Cosmetic and Toiletry Formulations, vol. 5, 2nd Edition, Copyright 1996.
Fontana, Anthony, J., "Water Activity: Why It Is Important for Food Safety," International Conference on Food Safety, Nov. 16-18, 1998, 9 pages.
Galligan, John et al., "Adhesive Polyurethane Liners for Anterior Restorations," J. Dent. Res., Jul.-Aug. 1968, pp. 629-632.
Gill, A.M, et al., "Adverse Drug Reactions in a Paediatric Intensitve Care Unit," Acta Paediatr 84:438-441, 1995.
Glaser, et al., Hyperhidrosis: A Comprehensive and Practical Approach to Patient Management, Expert Rev. Dermatol. 1(6), 773-775 (2006).
Gschnait, F., et al., "Topical Indomethacin Protects from UVB and UVA Irriadiation," Arch. Dermatol. Res. 276:131-132, 1984.
Hall, Karla, "Diaper Area Hemanglomas: A Unique Set of Concerns," members.tripod.com/~Michelle_G/diaper.html, Dec. 1, 2008, 8 pages.
Hashim, et al. "Tinea versicolor and visceral leishmaniasis," Int J Dermatol., Apr. 1994; 33(4), pp. 258-259.
Hepburn, NC., "Cutaneous leishmaniasis," Clin Exp Dermatol, Jul. 2000; 25(5), pp. 363-370.
Hill, Randall M. (Ed.) Silicone Surfactants, Table of Contents and Chapter 7, "Silicone Surfactants: Applicants in the Personal Care Industry," by David T. Floyd, 1999 (30 Pages).
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
International Search Report and Written Opinion, International Application No. PCT/IB2006/003628, Foamix Ltd., Dec. 7, 2007, 15 pages.
International Search Report and Written Opinion, International Application No. PCT/US2007/004459, Foamix Ltd., Dec. 9, 2008, 2 pages.
International Search Report for International Application No. PCT/IB2006/003974, Feb. 25, 2008 (3 pages).
International Search Report, International Patent Application No. PCT/IB2007/003463, Foamix, Ltd., Jul. 18, 2008, 3 pages.
International Search Report, International Patent Application No. PCT/IB2007/003759, Foamix Ltd., Jul. 8, 2008 (3 pages).
Kalkan, et al., The Measurement of Sweat Intensity Using a New Technique, Tr. J. of Medical Sciences 28, 515-517 (1998).
Kathon™ CG (product information sheet by Rohm and Haas, Jun. 2006).
Kinnunen, Contact Dermatitis Sep. 1989; 21(3): 154-8.
Koerber, S., "Humectants and Water Activity," Water Activity News, 2000, ISSN No. 1083-3943.
Licking Vaginal Dryness without a Prescription. Accessed www.estronaut.com/a/vag_dryness.htm on Dec. 14, 2008.
Martindale, The extra pharmacopoeia [28th] edition, Eds.: Reynolds, J.E.F. and Prasad, A.B., The Pharmaceutical Press, London, pp. 862-864, 1982.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merriam-Webster Online Dictionaary, 2008, "Mousse," Merriam-Webster Online, Dec. 8, 2008 www.merriam-webster.com/dictionary/mousse.
Metronidazole. www.usp.org/pdf/EN/veterinary/metronidazole.pdf. accessed Sep. 10, 2009, 4 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
OM Cinnamate. www.makingcosmetics.com/sunscreens/OM-Cinnamate-p102.html accessed Sep. 26, 2009.

Pendergrass, "The shape and dimensions of the human vagina as seen in three-dimensional vinyl polysiloxane casts," Gynecol Obstet. Invest. 1996:42(3):178-82.

Progesterone MSDS. www.usp.org.pdf.EN/referenceStandards/msds/1568007.pdf on Dec. 14, 2002, 5 pages.

Savin, et al., "Tinea versicolor treated with terbinafine 1% solution," Int J. Dermatol, Nov. 1999; 38(11), pp. 863-865.

Schmidt A., "Malassezia furfur: a fungus belonging to the physiological skin flora and its relevance in skin disorders," Curtis., Jan. 1997; 59(1), pp. 21-24.

Scott as Published in Pharmaceutical Dosage Forms; Disperse Systems, vol. 3, Copyright 1998.

Shear, et al., "Pharmacoeconomic analysis of topical treatments for tinea infections," Pharmacoeconomics. Mar. 1995; 7(3); pp. 251-267.

Sigma Aldrich, "HLB-Numbers in Lithography Nanopatterning," www.sigmaaldrich.com/materials-science/micro-and-nanoelectronics/lithography-nanopatterning/hlb-numbers.html, accessed: Feb. 2, 2009, pp. 1-3.

Sigma-Aldrich, Material Safety Data Sheet, Hydroxyethyl Cellulose, Mar. 3, 2004, 5 pages.

Skin Biology, CP Serum—Copper-Peptide Serum for Skin Regeneration and Reducing Wrinkles, Skin Biology, web.archive.org/web/20030810230608/http://www.skinbio.com/cpserum.html, Dec. 1, 2008, 21 pages.

Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat. Jun. 2002;13(2):51-60 (abstract only).

Tan et al., "Effect of Carbopol and Polyvinylpyrrolidone on the Mechanical, Rheological, and Release Properties of Bioadhesive Polyethylene Glycol Gels," AAPS PharmSciTech, 2000; 1(3) article 24 (2000), 10 pages.

Torres-Rodriguez, JM., "New topical antifungal drugs," Arch Med Res. 1993 Winter; 24(4), pp. 371-375.

Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid=0709F73D-A849-80CA-5FB784E866B576D1. Accessed Dec. 9, 2008.

"HLB Systems", pharmcal.tripod.com/ch17.htm, Accessed Sep. 17, 2010, pp. 1-3.

Adachi, Shuji. "Storage and Oxidative Stability of O/W/ Nano-emulsions." Foods Food Ingredients. J. Jpn. vol. 209, No. 11. 2004. 1 page.

Method: A Novel and General Concept, a New Template for Nanoencapsulation. University of Angers. Paris, France. No Date Listed. 2 pages.

Arct, et al., "Common Cosmetic Hydrophilic Ingredients as Penetration Modifiers of Flavonoids", International Journal of Cosmetic Science, 24(6):357-366 (2002)—Abstract, 1 page.

Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.

Austria, et al., "Stability of Vitamin C Derivatives in Solution and Topical Formulations", Journal of Pharmaceutical and Biomedical Analysis, 15:795-801 (1997).

Bernstein, et al., Effects of the Immunomodulating Agent R837 on Acute and Latent Herpes Simplex Virus Type 2 Invections, Antimicrobial Agents and Chemotherapy, 33(9):1511-1515 (1989).

Blute, "Phase behavior of alkyl glycerol ether surfacants", Physical Chemistry Tenside Sur. Det., 35(3):207-212 (1998).

Brenes, et al., "Stability of Copigmented Anthocyanins and Asorbics Acid in a Grape Juice Model System", J. Agric Food Chem, 53(1):49-56 (2005)—Abstract, 1 page.

Bronopol. Revtrieved online on Jun. 4, 2011. chemicalland21.com/specialtychem/perchem/BRONOPOL.html>. Jul. 17, 2006. 4 pages.

Buck, et al., "Treatment of Vaginal Intraephithelial Neoplasia (Primarily Low Grade) with Imiquimod 5% Cream", Journal of Lower Genetial Tract Disease, 7(3):290-293 (2003).

Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).

Burton, et al., "Hypertrichosis Due to Minoxidil", British Journal of Dermatology, 101:593-595 (1979).

Campos, et al., "Ascorbic Acid and Its Derivatives in Cosmetic Formulations", Cosmetics and Toiletries, 115(6):59-62 (2000)—Abstract, 1 page.

Carbowax 1000MSDS; www.sciencelab.com/xMSDS-Polyethylene.sub.--glycol.sub.-1000-9926-622. Accessed Dec. 13, 2008, 6 pages.

Carelli, et al., "Effect of Vehicles on Yohimbine Permeation Across Excised Hairless Mouse Skin", Pharm Acta Helv, 73(3):127-134 (1998)—Abstract, 1 page.

Chebil, et al., "Soulbility of Flavonoids in Organic Solvents", J. Chem. Eng. Data, 52(5):1552-1556 (2007)—Abstract, 1 page.

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

Chinnian, et al., "Photostability Profiles of Minoxidil Solutions", PDA J. Pharm Sci Technol., 50(2):94-98 (1996)—Abstract, 1 page.

Chollet, et al., "Development of a Topically Active Imiquimod Formulation", Pharmaceutical Development and Technology, 4(1):35-43 (1999).

Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.

Colloidal Silica. Retrieved online on Jun. 4, 2011. www.grace.com/engineeredmaterials/materialsciences/colloidalsilica/default.aspx>. Copyright 2011. 4 pages.

Croda. Aracel 165 Product Summary. 2011 (no month given). 1 page.

Dawber, et al., "Hypertrichosis in Females Applying Minoxidil Topical Solution and in Normal Controls", JEADV, 17:271-275 (2003).

Dentinger, et al., "Stability of Nifedipine in an Extemporaneously Compounded Oral Solution", American Journal of Health-System Pharmacy, 60(10):1019-1022 (2003)—Abstract, 1 page.

Disorder. (2007). In the American Heritage Dictionary of the English Language. Retrieved from www.credoreference.com/entry/hmdictenglang/disorder. 1 page.

Edens, et al., "Storage Stability and Safey of Active Vitamin C in a New Dual-Chamber Dispenser", Journal of Applied Cosmetology, 17(4):136-143 (1999)—Abstract, 1 page.

Edirisinghe, et al., "Effect of fatty acids on endothelium-dependent relaxation in the rabbit aorta", Clin Sci (Lond). Aug. 2006; 111(2): 145-51.

Edwards, "Imiquimod in Clinical Practice", J. Am Acad Dermatol., 43(1, Pt 2):S12-S17 (2000)—Abstract, 1 page.

English machine translation of JP-0816518 (1996) 9 pages.

English translation of abstract for Japanese Patent Publication No. 4892282 (1992) 1 page.

Esposito, E. et al. "Nanosystems for Skin Hydration: A Comparative Study." International Journal of Cosmetic Science. 29. 2007. pp. 39-47.

Ethylene Oxide Derivatives: An Essence of Every Industry. A definition of Emulsifier. www.emulsifiers.in/ethylene_oxide_derivatives2.htm. Accessed Jul. 12, 2011. 3 pages.

Farahmand, et al., "Formulation and Evaluation of a Vitamin C Multiple Emulsion", Pharmaceutical Development and Technology, 11(2):255-261 (2006)—Abstract, 1 page.

Final Office Action for U.S. Appl. No. 11/430,437, Tamarkin et al., Dec. 16, 2008, 24 pages.

Fonatana, Anthony J., "Water Activity: Why It is Important for Food Safety," International Conference on Food Safety, Nov. 16-18, 1998, pp. 177-185.

Gallarate, et al., "On the Stability of Ascorbic Acid in Emulsified Systems for Topical and Cosmetic Use", International Journal of Pharmaceutics, 188:233-241 (1999).

Gladkikh, "Ascorbic Acid and Methods of Increasing its Stability in Drugs", Translated from Khimiko-Farmatsevticheskii Zhurnal, 4(12):37-42 (1970)—1 page.

Graves, S. et al. "Structure of Concentrated Nanoemulsions." The Journal of Chemical Physics.. 122 America Institute of Physics. Published Apr. 1, 2005. 6 pages.

Groveman, et al., "Lack of Efficacy of Polysorbate 60 in the Treatment of Male Pattern Baldness", Arch Intern Med, 145:1454-1458 (1985).

Hakan, et al., "The protective effect of fish oil enema in acetic acid and ethanol induced colitis," The Turkish Journal of Gasroenterology, 2000, vol. 11, No. 2, pp. 155-161.

Hallstar. Retrieved online on Jun. 4, 2011. www.hallstar.com/pis.php?product=1H022>. 1 page.

Harrison, et al., "Effects of cytokines and R-837, a cytokine inducer, on UV-irradiation augmented recurrent genital herpes in guinea pigs", Antivial Res., 15(4):315-322 (1991).

Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Heart Failure, The Merck Manual, 2008 www.merck.com/mmhe/sec03/ch025/ch025a.html>> 12 pages.

babydoc.com/online/diseaseeczema.asp., Atopic Dermatitis, Copyright 2000, 6 pages.

web.archive.org/web/20000106225413/http://pharmacy.wilkes.edu/kibbeweb/lab7.html, Characteristics of Surfactants and Emulsions, Jan. 29, 2010, 5 pages.

www.agworkshop.com/p3.asp, AG&Co. Essential oil workshop. 1 page. Accessed Jan. 31, 2010.

Hubbe, Martin. Mini-Encyclopedia of Papermaking Wet-End Chemistry: Additives and Ingredients, their Composition, Functions, Strategies for Use. Retrieved online on Jun. 4, 2011. www4.ncsu.edu/~hubbe/CSIL.htm>. Feb. 1, 2001. 2 pages.

ICI Americas Inc. "The HLB System: A Time-Saving Guide to Emulsifier Selection." Mar. 1980. pp. 1-22.

Ikuta, et al., "Scanning Electron Microscopic Observation of Oil/Wax/Water/Surfacant System", Journal of SCCJ, 34(4):280-291 (2004)—Abstract, 1 page.

Indomethacin. Retrieved online on Jun. 3, 2011. it03.net/com/oxymatrine/down/1249534834.pdf>. Aug. 15, 2009. 3 pages.

International Search Report and Written Opinion for International Application No. PCT/IB10/02241 mailed Feb. 10, 2011. 9 pages.

International Search Report and Written Opinion for International Application No. PCT/IB10/02613 mailed Mar. 16, 2011. 9 pages.

International Search Report and Written Opinion for International Application No. PCT/IB10/02617 mailed Mar. 15, 2011. 10 pages.

International Search Report and Written Opinion, International Patent Application No. PCT/IB2006/004026, Foamix, Ltd., May 20, 2008, 17 pages.

International Search Report from PCT/IB2006/003519 , Mailed Dec. 3, 2007. 1 page.

Invitation to Pay Additional Fees for International Application No. PCT/IB2009/005012 mailed Jul. 27, 2010. 13 pages.

Izquierdo, P. et al. "Formation and Stability of Nano-Emulsions Prepared Using the Phase Inversion Temperature Method." University of Barcelona. Sep. 17, 2001. 1 page.

Kanamoto, et al., "Pharmacokinetics of two rectal dosage forms of ketoprofen in patients after anal surgery," J Pharmacobiodyn., Mar. 1988; 11(3):141-5.

Kang,et al., "Enhancement of the Stability and Skin Penetration of Vitamin C by Polyphenol", Immune Netw., 4(4):250-254 (2004)—Abstract, 1 page.

Karasu, T.B. et al., "Treatment of Patients with Major Depressive Disorder, Second Edition," pp. 1-78, 2000.

Kim, "Stability of Minoxidil in Aqueous Solution", Yakhak Hoechi, 30(5):228-231 (1986)—Abstract, 1 page.

Kleber, M.D., H.D. et al., "Treatment of Patients with Substance Use Disorders, Second Edition," pp. 1-276, 2006.

Kreuter, J. "Nanoparticles and microparticles for drug and vaccine delivery," J. Anat. (1996) 189, pp. 503-505.

Kumar, J. et ak., "Application of Broad Spectrum Antiseptic Povidone Iodine as Powerful Action: A Review," Journal of Pharmaceutical Science and Technology vol. 1(2), 2009, 48-58.

Kwak et al. "Study of Complete Transparent Nano-Emulsions which Contain Oils." IFSCC Conference 2003, Seoul, Korea, Sep. 22-24, 2003. 3 pages.

Lautenschlager, Dr. Hans. "A Closer Look on Natural Agents: Facts and Future Aspects." Kosmetic Konzept. Kosmetische Praxis. 2006 (no month given). (5), 8-10. 3 pages.

Lebwohl et al. "Treatment of Psoriasis. Part 1. Topical Therapy and Phototherapy." J. Am. Acad. Dermatol. 45:487-498. Oct. 2001.

Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).

Leung, et al., "Bioadhesive Drug Delivery in Water-Soluble Polymers," American Chemical Society, Chapter 23, 1991, pp. 350-366.

Li, et al., "Solubility Behavior of Imiquimod in Alkanoic Acids", Abstract 3029, Pharmaceutical Research, vol. 14, No. 11 Supplemental (November), p. S475 (1997), 2 pages.

Lippacher, A. et al. "Liquid and Semisolid SLN Dispersions for Topical Application" Rheological Characterization. European Journal of Pharmaceutics and Biopharmaceutics. 58. 2004. pp. 561-567.

Lupo, "Antioxidants and Vitamins in Cosmetics", Clinics in Dermatology, 19:467-473 (2001).

Merck Index, An Encyclopedia of Chemicals, Drugs, and Biologicals. 13th Edition. O'Neil et al eds. Entries 1058, 2350, 6143, and 8803. 2001. 7 pages.

Merriam Webster Online Dictionary [online] retrieved from www.merriam-webster.com/cgi-bin/dictionary?book=dictionary &va=derivative on Jul. 5, 2008; 1 page.

Messenger, et al., "Minoxidil: Mechanisms of Action on Hair Growth", British Journal of Dermatology, 150:186-194 (2004).

Metz, et al., "A Phase I Study of Topical Tempol for the Prevention of Alopecia Induced by Whole Brain Radiotherapy", Clinical Cancer Research, 10:6411-6417 (2004).

Meucci, et al., "Ascorbic Acid Stability in Aqueous Solutions", Acta Vitaminol Enzymol, 7(3-4):147-153 (1985)—Abstract, 1 page.

MMP Inc. International Development and Manufacturing, "Formulating specialities," mmpinc.com, 3 pages. Feb. 2, 2010.

Molan, Peter Clark, "World Wide Wounds," Dec. 2001, 13 pages.

"Opitmization of Nano-Emulsions Production by Microfluidization." European Food Research and Technology. vol. 225, No. 5-6. Sep. 2007. Abstract. 1 page.

Office Action for U.S. Appl. No. 11/430,437, Tamarkin et al., May 9, 2008, 27 pages.

Office Action received from the U.S. Patent Office, U.S. Appl. No. 11/430,599, Jul. 28, 2008 (59 pages).

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

Pakpayat, et al., "Formulation of Ascorbic Acid Microemulstions with Alkyl Polyglycosides", European Journal of Pharmaceutics and Biopharmaceutics, 72:444-452 (2009).

Paula. ww.cosmeticscop.com/cosmetic-ingredient-dictionary/definition/259/c12-15-alkyl-benzoate.aspx. Printed Oct. 24, 2010. 1 page.

PCT Search Report and Written Opinion for International Application No. PCT/IB2010/001126 mailed Apr. 20, 2011, 12 pages.

Prescription Information for Aldara, Mar. 2007 (29 pages).

Prevent. (2007). In The American Heritage Dictionary of the English Language. Retrieved from www.credoreference.com/entry/hmdictenglang/prevent. 1 page.

Psoriasis, www.quickcare.org/skin/causes-of0psoriasis.html. Accessed Sep. 9, 2010—3 pages.

Purcell, Hal C. "Natural Jojoba Oil Versus Dryness and Free Radicals." Cosmetics and Toiletries Manufacture Worldwide. 1988. 4 pages.

Raschke, et al., "Topical Activity of Ascorbic Acid: From in Vitro Optimization to in Vivo Efficacy", Skin Pharmacology and Physiology, 17(4):200-206 (2004)—Abstract, 1 page.

Raymond, Iodine as an Aerial Disinfectant, Journal of Hygiene, vol. 44, No. 5 (May 1946), pp. 359-361.

Receptacle. Merriam Webster. www.merriam-webster.com/dictionary/receptacle. Accessed Jul. 12, 2011. 1 page.

Richwald, "Imiquimod", Drugs Today, 35(7):497 (1999)—Abstract, 1 page.

Rieger and Rhein. "Emulsifier Selection/HLB." Surfactants in Cosmetics. 1997 (no month given). 1 page.

Rosacea, clinuvel.com/skin-conditions/common-skin-conditions/rosacea#h0-6-prevention. Accessed Sep. 9, 2010, 5 pages.

Schutze, M.D., Harry "Iodine and Sodium Hypochlorite as Wound Disinfectants," The British Medical Journal, pp. 921-922, 1915.

Scientific Discussion for the approval of Aldara, EMEA 2005 (10 pages).

Seborrheic Dermatitis, www.cumc.columbia.edu/student/health/pdf/R-S/Seborrhea%20Dermatitis.pdf. Access Sep. 9, 2010, 2 pages.

Shear, et al., "Pharmacoeconomic analysis of topical treatments for tinea infections," Pharmacoeconomics. Mar. 1995; 7(3); pp. 251-267. 2 pages.

Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.

Shim, et al., "Transdermal Delivery of Mixnoxidil with Block Copolymer Nanoparticles", J. Control Release, 97(3):477-484 (2004)—Abstract, 1 page.

Silicone. Definition. Retrieved Apr. 19, 2011 from www.oxforddictionaries.com/definition/silicone?view=uk. 1 page.

Simovic, S. et al., "The influence of Processing Variables on Performance of O/W Emulsion Gels Based on Polymeric Emulsifier (Pemulen ÒTR-2NF)," International Journal of Cosmetic Science, vol. 2(2): abstract only. Dec. 24, 2001, 1 page.

Skin Deep Cosmetics. PPG-40-PEG-60 Lanolin Oil www.cosmeticsdatabase.com/ingredient/722972/PPG-40-PEG-60_Lanolin_Oil/?ingred06=722972. Accessed May 19, 2010. 3 pages.

Sonneville-Aubrun, O. et al. "Nanoemulsions: A New Vehicle for Skincare Products." Advances in Colloid and Interface Science. 108-109. 2004. pp. 145-149.

Sreenivasa, et al., "Preparation and Evaluation of Minoxidil Gels for Topical Application in Alopecia", Indian Journal of Pharmaceutical Sciences, 68(4):432-436 (2006), 11 pages.

Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.

Surfactant. Wikipedia—en.wikipedia.org/wiki/surfactant. Printed Oct. 24, 2010. 1 page.

Sweetman, Sean C. Martindale: The Complete Drug Reference. 33rd Edition. London. Pharmaceutical Press. Jun. 21, 2002. pp. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tanhehco, "Potassium Channel Modulators as Anti-Inflammatory Agents", Expert Opinion on Therapeutic Patents, 11(7):1137-1145 (2001)—Abstract, 3 pages.

Tarumoto, et al., Studies on toxicity of hydrocortisone 17-butyrate 21-propionate—1. Accute toxicity of hydrocortisone 17-butyrate 21-propionate and its analogues in mice, rats and dogs (author's trans), J Toxicol Sci., Jul. 1981; 6 Suppl: 1-16.

Tata, et al., "Penetration of Minoxidil from Ethanol Propylene Glycol Solutions: Effect of Application Volume on Occlusion", Journal of Pharmaceutical Sciences, 84(6):688-691 (1995).

Tata, et al., "Relative Influence of Ethanol and Propylene Glycol Cosolvents on Deposition of Minoxidil into the Skin", Journal of Pharmaceutical Sciences, 83(10):1508-1510 (1994).

Trofatter, "imiquimod in clinical Practice", European Journal of Dermatology, 8(7 Supp.):17-19 (1998)—Abstract, 1 page.

Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.

Tsai, et al., "Effect of Minoxidil Concentration on the Deposition of Drug and Vehicle into the Skin", International Journal of Pharmaceutics, 96(1-3):111-117 (1993)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Wermuth, C.G. "Similarity in drugs: reflections on analogue design," Drug Discovery Today, vol. 11, Nos. 7/8, Apr. 2006, pp. 348-354.

Williams, "Scale up of an olive/water cream containing 40% diethylene glycol momoethyl ether", Dev. Ind. Pharm., 26(1):71-77 (2000).

Wormser et al., Protective effect of povidone-iodine ointment against skin lesions induced by sulphur and nitrogen mustards and by non-mustard vesicants, Arch. Toxicol., 1997, 71, 165-170.

Wormser, Early topical treatment with providone-iodine ointment reduces, and sometimes prevents, skin damage following heat stimulus, Letter to the Editor, Burns 24, pp. 383, 1998.

* cited by examiner

FOAMABLE COMPOSITIONS, KITS AND METHODS FOR HYPERHIDROSIS

CROSS-REFERENCE TO RELATED APPLICATIONS

This application claims the benefit under 35 U.S.C. §119 (e) of U.S. Provisional Patent Application No. 60/781,868, filed on Mar. 13, 2006, entitled Foamable Composition for Hyperhidrosis, and is incorporated herein by reference in its entirety.

This application claims the benefit under 35 U.S.C. §119 (e) of U.S. Provisional Patent Application No. 60/897,638, filed Jan. 26, 2007, entitled Quiescent Foamable Compositions, Steroids, Kits And Uses Thereof, and is incorporated herein by reference in its entirety.

This application claims the benefit under 35 U.S.C. §119 (e) of U.S. Provisional Patent Application No. 60/899,176, filed Feb. 2, 2007, entitled Non-Alcoholic Foamable Petrolatum Based Pharmaceutical and Cosmetic Compositions and Their Uses, and is incorporated herein by reference in its entirety.

This application is a continuation-in-part application of co-pending U.S. patent application Ser. No. 10/911,367, filed on Aug. 4, 2004, which claims the benefit of priority under 35 U.S.C. §119(e) to U.S. Patent Application Ser. No. 60/492,385, filed on Aug. 4, 2003, both entitled "Foam Carrier Containing Amphiphilic Copolymer Gelling Agent" and both are incorporated herein in their entirety by reference.

This application is a continuation-in-part application of co-pending U.S. patent application Ser. No. 11/078,902, filed on Mar. 11, 2005, entitled Nonsteroidal Immunomodulating Kit and Composition and Uses Thereof, and is incorporated in its entirety by reference.

This application is a continuation-in-part application of co-pending U.S. patent application Ser. No. 10/532,618, filed on Dec. 22, 2005, which is an application filed under 35 U.S.C. §371 of International Patent Application No. IB03/005527 designating the United States and filed on Oct. 24, 2003, which claims the benefit of priority under 35 U.S.C. §119(e) to U.S. Patent Application Ser. No. 60/492,546, filed on Nov. 29, 2002, both entitled "Cosmetic and Pharmaceutical Foam," and which also claims the benefit of priority under 35 USC §119(a) to Israeli Patent App. No. 152486, filed Oct. 25, 2002, all of which are hereby incorporated in their entirety by reference.

BACKGROUND OF THE INVENTION

Foams and, in particular, foam emulsions are complex dispersion systems which do not form under all circumstances. Slight shifts in foam emulsion composition, such as by the addition of active ingredients, may destabilize the foam.

Hyperhidrosis is a medical condition characterized by excessive sweating in the armpits, palms, soles of the feet, face, scalp, and/or torso. Hyperhidrosis involves sweating in excess of the amount required normally for the body's level of activity and temperature. There are two types of hyperhidrosis—primary and secondary. In primary hyperhidrosis, the cause is unknown and excessive sweating is localized in the armpits, hands, face, and/or feet. Primary hyperhidrosis begins during childhood or early adolescence, gets worse during puberty, and lasts a lifetime. In secondary hyperhidrosis, which is less common than primary hyperhidrosis, excessive sweating is caused by another medical condition and usually occurs over the entire body. Medical conditions that can cause secondary hyperhidrosis include hyperthyroidism, menopause, obesity, psychiatric disorders, and diabetes. Secondary hyperhidrosis may also be caused by use of certain medications.

Topical agents applied to the skin in the affected area are the first course of treatment for hyperhidrosis. Topical applications include anticholinergic drugs, boric acid, tannic acid, resorcinol, potassium permanganate, formaldehyde, glutaraldehyde and methenamine. Antiperspirant actives currently used in the industry are Lewis acids. Typically, such antiperspirant actives are partially neutralized chloride salts of metal ions such as aluminum and zirconium.

U.S. Pat. No. 6,433,003 discloses methods for treating hyperhidrosis involving the topical administration of glycopyrrolate compounds to humans. U.S. Pat. Nos. 5,730,964 and 5,512,555 teach methods of treating sweat related conditions with compounds that are 5-alpha-reductase inhibitors, such as finasteride, episteride and cholestan-3-one, alone or in combination with other active agents to treat conditions such as apocrine gland sweating, hyperhidrosis, and hydradenitis suppurativa. U.S. Pat. No. 4,885,282 describes a method for the treatment of skin suffering from hyperhidrosis, ichthyosis or wrinkling, comprising applying to the affected area of a compound selected from the group consisting of mono- and dicarboxylic acids having 4 to 18 carbon atoms, a mercapto derivative thereof, a salt thereof, and an ester thereof.

US Pat. Application No. 20050196414 describes a method of administering a botulinum toxin to a subject comprising topically applying to the skin or epithelium of the subject the botulinum toxin for prevention or reduction of symptoms associated with subjective or clinical hyperhidrosis. US Pat. App. No. 20040192754 teaches compounds that can ameliorate symptoms of idiopathic hyperhidrosis and associated conditions include 5-HT2C receptor antagonists (i.e., ketanserin, ritanserin, mianserin, mesulergine, cyproheptadine, fluoxetine, mirtazapine, olanzapine, and ziprasidone) as well as 5-HT2C receptor modulators (i.e., inverse agonists, partial agonists, and allosteric modulators).

SUMMARY OF THE INVENTION

The present invention relates to foamable carriers, compositions and foams comprising an active agent and which are suitable for use in relation to ameliorating or reducing perspiration especially excessive sweating or hyperhidrosis.

The present invention further relates to the use of different platforms as a vehicle for delivering an effective amount of a hyperhidrosis agent to a target site.

The present invention further relates to a hyperhidrosis kit and method of use in presenting different platforms as a vehicle for delivering an effective amount of a hyperhidrosis agent to a target site.

According to preferred embodiments of the present invention, there is provided various compositions geared towards treating hyperhidrosis or any condition involving and/or promoting excessive sweating, typically involving the whole body, include hyperthyroidism or similar endocrine disorders; endocrine treatment for prostatic cancer or other types of malignant disorder; severe psychiatric disorders; obesity and menopause. The foamable compositions of the present invention are suitable for treating palmar hyperhidrosis; axillary hyperhidrosis; plantar hyperhidrosis; hyperhidrosis of the trunk and/or the thighs; and facial hyperhidrosis; and any combination of them consisting of a therapeutic foamable composition including an active agent, suitable for the treatment or prevention of hyperhidrosis.

According to one or more embodiments of the present invention, there is provided an oil in water emulsion formulation as a suitable vehicle for hyperhidrosis agents.

According to one or more embodiments of the present invention, there is provided a water in oil emulsion formulation as a suitable vehicle for hyperhidrosis agents.

According to one or more embodiments of the present invention, there is provided a petrolatum in water emulsion formulation as a suitable vehicle for hyperhidrosis agents.

According to one or more embodiments of the present invention, there is provided a petrolatum waterless formulation as a suitable vehicle for hyperhidrosis agents.

According to one or more embodiments of the present invention, there is provided waterless oleaginous formulation as a suitable vehicle for hyperhidrosis agents.

According to one or more embodiments of the present invention, there is provided a waterless polyethylene glycol formulation as a suitable vehicle for hyperhidrosis agents.

According to one or more embodiments of the present invention, there is provided a formulation as a suitable vehicle for hyperhidrosis agents comprising a) a solvent;

b) a surfactant;

c) a hyperhidrosis agent;

d) one or more optional agents selected from the group comprising a surfactant, co-emulsifier or foam stabilizer; a polymeric agent; a viscosity, bulking or firming agent; a stabilizer; a foam adjuvant; a co-solvent; a penetration enhancer; a modulating agent; and an agent capable of having an occlusive effect;

e) a propellant;

wherein the presence of an aluminum salt or other hyperhidrosis agent in a composition does not prevent a foam of good or satisfactory quality from being produced and wherein the composition is stored in an aerosol container and upon release expands to form a breakable foam.

According to one or more embodiments of the present invention, there is provided an emulsion formulation as a suitable vehicle for hyperhidrosis agents comprising;

f) a solvent;

g) a surfactant h) a hyperhidrosis agent;

i) one or more optional agents selected from the group comprising a surfactant, co-emulsifier or foam stabilizer; a polymeric agent; a viscosity, bulking or firming agent; a stabilizer; a foam adjuvant; a co-solvent; a penetration enhancer; a modulating agent; and an agent capable of having an occlusive effect;

j) a propellant;

wherein the presence of an aluminum salt or other hyperhidrosis agent in a composition does not prevent a foam of good or satisfactory quality from being produced and wherein the composition is stored in an aerosol container and upon release expands to form a breakable foam and wherein the composition has some or partial resistance to creaming when subjected to centrifugation at 3000 rpm for 10 minutes.

By some or partial resistance to creaming it is intended that after centrifugation the emulsion displays no, some or partial creaming or does not separate into two separate phases.

According to yet further embodiments of the present invention, the foamable composition is substantially alcohol-free.

According to yet further embodiments of the present invention, the foamable composition additionally comprises a humectant.

According to yet further embodiments of the present invention, the foamable composition additionally comprises a moisturizer.

According to yet further embodiments of the present invention, the foamable composition is substantially resistant to creaming at least to some or a partial degree when subjected to centrifugation at 3000 RPM for 10 minutes. In other words the composition does not display phase separation.

According to further embodiments of the present invention, the active agent is selected from the group consisting of an anticholinergic drugs, an agent, selected from the group consisting of boric acid, tannic acid, resorcinol, potassium permanganate, formaldehyde, glutaraldehyde and methenamine, a Lewis acid, a salt or a complex of a metal ion, capable of treating hyperhidrosis, a salt or a complex of a metal ion such as aluminum and zirconium, a salt or a complex of a metal selected from the group consisting of aluminum and zirconium, a 5-alpha-reductase inhibitor, an agent, selected from the group consisting of finasteride, flutamide, spironolactone, saw palmetto extract, epristeride and cholestan-3-one, an agent, capable of treating hyperhidrosis, selected from the group consisting of mono- and dicarboxylic acids having 4 to 18 carbon atoms, a mercapto derivative thereof, a salt thereof, and an ester thereof, botulinum toxin, a 5-HT2C receptor antagonist, an agent, selected from the group consisting of ketanserin, ritanserin, mianserin, mesulergine, cyproheptadine, fluoxetine, mirtazapine, olanzapine, and ziprasidone, and a 5-HT2C receptor modulator, an antiperspirant.

According to still further embodiments of the present invention, the foamable composition further comprises at least one additional therapeutic agent selected from the group consisting of an anti-infective, an antibiotic, an antibacterial agent, an antifungal agent, an antiviral agent, an antiparasitic agent, a steroid, a non-steroidal antiinflammatory agent, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, an anti wrinkle agent, a skin whitening agent, a skin protective agent, a masking agent, an anti-wart agent, a refatting agent, a lubricating agent and any mixture thereof.

According to yet further embodiments of the present invention, the concentration of the surface active agent is between about 0.1% and about 5%.

According to further embodiments of the present invention, the polymeric agent is selected from the group consisting of a water-soluble cellulose ether and a naturally-occurring polymeric material.

According to yet further embodiments of the present invention, the water-soluble cellulose ether is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose, carboxymethylhydroxyethylcellulose, xanthan gum, guar gum, carrageenin gum, locust bean gum and tragacanth gum.

According to further embodiments of the present invention, there is provided a method of treating, alleviating or preventing a disorder of the skin, a body cavity or mucosal surface, wherein the disorder involves excessive sweating as one of its symptoms, including a foamed composition administering topically to a subject having the disorder, the foamed composition including an active agent, suitable for the treatment or prevention of hyperhidrosis, about 2% to about 50% by weight of an organic carrier selected from the group consisting of a hydrophobic organic carrier, a polar solvent, an emollient and any mixture thereof, about 0.1% to about 5% by weight of a surface-active agent, about 0.01% to about 5% by weight of a polymeric additive selected from the group consisting of a bioadhesive agent, a gelling agent, a film forming agent and a phase change agent, and water, wherein the active agent is administered in a therapeutically effective amount.

According to further embodiments of the method according present invention, the composition further comprises about 0.1% to about 5% by weight of a foam adjuvant is selected from the group consisting of a fatty alcohol having 15 or more carbons in their carbon chain, a fatty acid having 16 or more carbons in their carbon chain, fatty alcohols, derived from beeswax and including a mixture of alcohols, a majority of which has at least 20 carbon atoms in their carbon chain, a fatty alcohol having at least one double bond, a fatty acid having at least one double bond, a branched fatty alcohol, a branched fatty acid, a fatty acid substituted with a hydroxyl group, cetyl alcohol, stearyl alcohol, arachidyl alcohol, behenyl alcohol, 1-triacontanol, hexadecanoic acid, stearic acid, arachidic acid, behenic acid, octacosanoic acid, 12-hydroxy stearic acid and any mixture thereof.

According to still further embodiments of the method according present invention, the composition further comprises at least one additional therapeutic agent.

According to still further embodiments of the method according present invention, the disorder is selected from the group consisting of a dermatose, a dermatitis, a vaginal disorder, a vulvar disorder, an anal disorder, a disorder of a body cavity, an ear disorder, a disorder of the nose, a disorder of the respiratory system, a bacterial infection, fungal infection, viral infection, dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

DETAILED DESCRIPTION OF THE INVENTION

The present invention provides a foamable therapeutic composition for administration to the skin, a body surface, a body cavity or mucosal surface, e.g., the mucosa of the nose, mouth, eye, ear, respiratory system, vagina or rectum (severally and interchangeably termed herein "target site") for the treatment of hyperhidrosis. The foamable therapeutic composition includes (1) at least one active agent suitable for the treatment or prevention of hyperhidrosis; and (2) at least one foamable composition platform selected from the group consisting of an oil in water emulsion; a water in oil emulsion; a petrolatum in water emulsion; a petrolatum waterless formulation; a waterless oleaginous formulation and a waterless polyethylene glycol or propylene glycol based composition.

According to one or more embodiments of the present invention, there is also provided a hyperhidrosis kit comprising at least a first hyperhidrosis composition in an aerosol container accommodating a pressurized product and having an outlet capable of releasing the pressurized product as a foam and at least a second hyperhidrosis composition in an aerosol container accommodating a pressurized product and having an outlet capable of releasing the pressurized product as a foam.

The first and second compositions are different from one another and are independently selected from the group consisting of an oil in water emulsion; a water in oil emulsion; a petrolatum in aqueous emulsion; a petrolatum waterless formulation; a waterless oleaginous formulation and a waterless polyethylene glycol or propylene glycol based composition comprising at least one active agent, suitable for the treatment or prevention of hyperhidrosis.

According to one or more embodiments of the present invention, there is also provided a hyperhidrosis kit comprising at least a first hyperhidrosis composition in an aerosol container accommodating a pressurized product and having an outlet capable of releasing the pressurized product as a foam and at least a second hyperhidrosis composition in an aerosol container accommodating a pressurized product and having an outlet capable of releasing the pressurized product as a foam wherein the first composition is selected from the group consisting of an oil in water emulsion; a water in oil emulsion; a petrolatum in aqueous emulsion; a petrolatum waterless formulation; a waterless oleaginous formulation; and a waterless polyethylene glycol or a waterless propylene glycol based composition, said first composition comprising a first active agent, suitable for the treatment or prevention of hyperhidrosis wherein the second composition is selected from the group consisting of an oil in water emulsion; a water in oil emulsion; a petrolatum in aqueous emulsion; a petrolatum waterless formulation; a waterless oleaginous formulation; and a waterless polyethylene glycol or a waterless propylene glycol based composition, said second composition comprising a second active agent, suitable for the treatment or prevention of hyperhidrosis.

In one or more embodiments, the second composition is selected from a platform that is other than the platform selected for the first composition.

In one or more embodiments, the first composition is selected from the group consisting of an oil in water emulsion; a water in oil emulsion; a petrolatum in aqueous emulsion; said first composition comprising at least one active agent, suitable for the treatment or prevention of hyperhidrosis, and the second composition is selected from the group consisting of a petrolatum waterless formulation; a waterless oleaginous formulation; and a waterless polyethylene glycol or a waterless propylene gylcol based composition, said second composition comprising at least one active agent, suitable for the treatment or prevention of hyperhidrosis.

In one or more embodiments, the first composition is selected from the group consisting of an oil in water emulsion; a water in oil emulsion; a petrolatum in aqueous emulsion; said first composition comprising a first active agent, suitable for the treatment or prevention of hyperhidrosis, and the second composition is selected from the group consisting of a petrolatum waterless formulation; a waterless oleaginous formulation; and a waterless polyethylene glycol or a waterless propylene gylcol based composition, said second composition comprising a second active agent, suitable for the treatment or prevention of hyperhidrosis.

According to one or more embodiments of the present invention, there is also provided a hyperhidrosis kit comprising a dual aerosol dispenser and a dispenser head for use with the dual aerosol dispenser. The dual aerosol dispenser comprises two aerosol containers, wherein a first composition is contained in a first container and a second composition is contained in a second container.

The dispenser head of the dual aerosol dispenser comprises an actuator, wherein the dispensing head is structured and positioned to be an actuator or comprises an actuator button disposed within the dispensing head to simultaneously actuate the plurality of containers, and a flow guide. The flow guide comprises a plurality of flow conduits disposed within the flow guide. Each of the plurality of flow conduits includes an inlet through a wall of the flow guide connecting with a flow conduit and an outlet from a flow conduit through a wall of the flow guide.

Each of the plurality of inlets and containers has a linker to link an inlet and a container so as to allow the contents of the container upon actuation to pass through the inlet and through the flow conduit to reach and pass through the outlet.

The flow guide is structured and positioned to allow simultaneous flow communication between each of the plurality of flow conduits and wherein the plurality of outlets are structured and positioned to allow substantially contemporaneously dispensing and/or combining of the content from a plurality of containers external to the dispensing head. Further details of a dual aerosol dispenser for use with a foamable hyperhidrosis composition is found in co-pending, co-owned U.S. patent application Ser. No. 11/520,473, entitled "Apparatus and Method for Releasing a Measure of Content from a Plurality of Containers," the contents of which are incorporated in its entirety by reference.

According to one or more embodiments of the present invention, there is also provided a hyperhidrosis kit wherein at least one canister includes a metered dosing means for repeatedly delivering a unified quantified dose of foam.

According to one or more embodiments of the present invention, there is also provided a hyperhidrosis kit wherein each canister includes a metered dosing means for repeatedly delivering a unified quantified dose of foam. Further details of a metered dosing means suitable for use with foamable hyperhidrosis composition is found in co-pending, co-owned U.S. patent application Ser. No. 11/406,133, entitled "Apparatus and Method for Releasing a Measured Amount of Content from a Container," the contents of which are incorporated in its entirety by reference.

According to one or more embodiments of the present invention, there is also provided a method of using a hyperhidrosis kit wherein a subject in need applies a first hyperhidrosis composition to a target area and then applies a second hyperhidrosis composition to the target area. in one or more embodiments, the second hyperhidrosis composition is applied to the target area after allowing for the first composition to be substantially absorbed.

In one or more embodiments, the first and second compositions are different and are selected from the group consisting of an oil in water emulsion; a water in oil emulsion; a petrolatum in aqueous emulsion; a petrolatum waterless formulation; a waterless oleaginous formulation and a waterless polyethylene glycol or propylene glycol based composition comprising) at least one active agent, suitable for the treatment or prevention of hyperhidrosis.

In one or more embodiments, the first composition is selected from the group consisting of an oil in water emulsion; a water in oil emulsion; a petrolatum in aqueous emulsion; a petrolatum waterless formulation; a waterless oleaginous formulation; and a waterless polyethylene glycol or a waterless propylene glycol based composition, said first composition comprising a first active agent, suitable for the treatment or prevention of hyperhidrosis; and wherein the second composition is selected from the group consisting of an oil in water emulsion; a water in oil emulsion; a petrolatum in aqueous emulsion; a petrolatum waterless formulation; a waterless oleaginous formulation; and a waterless polyethylene glycol or a waterless propylene glycol based composition, said second composition comprising a second active agent, suitable for the treatment or prevention of hyperhidrosis.

It may be that an individual in need has dry skin and therefore applying an emollient or moisturizing formulation may be advantageous. It may also possibly be advantageous to apply a waterless formulation first followed by an emollient or petrolatum or oleaginous composition thereafter. Likewise if a subject in need has greasy or oily skin then it may possibly be advantageous to apply an emollient or petrolatum or oleaginous composition waterless formulation first followed by a waterless composition thereafter.

According to one or more embodiments of the present invention, there is also provided a method of using a hyperhidrosis kit wherein a subject in need applies a first hyperhidrosis composition to a target area and then applies a second hyperhidrosis composition to the target area after allowing for the first composition to be substantially absorbed wherein the first composition is selected from the group consisting of an oil in water emulsion; a water in oil emulsion; a petrolatum in aqueous emulsion; said first composition comprising at least one active agent, suitable for the treatment or prevention of hyperhidrosis wherein the second composition is selected from the group consisting of a petrolatum waterless formulation; a waterless oleaginous formulation; and a waterless polyethylene glycol or a waterless propylene glycol based composition, said second composition comprising at least one active agent, suitable for the treatment or prevention of hyperhidrosis.

According to one or more embodiments of the present invention, there is also provided a method of using a hyperhidrosis kit wherein a subject in need applies a first hyperhidrosis composition to a target area and then applies a second hyperhidrosis composition to the target area after allowing for the first composition to be substantially absorbed wherein the first composition is selected from the group consisting of an oil in water emulsion; a water in oil emulsion; a petrolatum in aqueous emulsion; said first composition comprising a first active agent, suitable for the treatment or prevention of hyperhidrosis wherein the second composition is selected from the group consisting of a petrolatum waterless formulation; a waterless oleaginous formulation; and a waterless polyethylene glycol or a waterless propylene glycol based composition, said second composition comprising a second active agent, suitable for the treatment or prevention of hyperhidrosis.

According to one or more embodiments of the present invention the hyperhidrosis composition is a combination of active agents.

According to one or more embodiments of the present invention the hyperhidrosis composition is a combination of active agents which are synergistic.

According to one or more embodiments of the present invention the first hyperhidrosis composition comprises a first hyperhidrosis agent and the second hyperhidrosis composition comprises a second hyperhidrosis agent wherein the first and second hyperhidrosis agents work in combination.

According to one or more embodiments of the present invention the first hyperhidrosis composition comprises moisture absorbers or film forming agent and the second hyperhidrosis composition comprises moisturizers or humectants or vica versa; wherein the first and second hyperhidrosis agents work in combination. In this connection a moisture absorber can comprise for example a hygroscopic solvent or a polymeric agent Hyperhidrosis is a personal and individual condition. Also subjects in need have varying skin types and conditions. It therefore follows that certain types of platform compositions will be more suitable depending on the individual concerned. Thus there is provided a hyperhidrosis kit and a method of using the kit to identify which platform compositions provide more effective relief to the subject in need.

According to one or more embodiments of the present invention, there is also provided a method of using a hyperhidrosis kit wherein a subject in need applies a first hyperhidrosis composition to a first target area and then applies a second hyperhidrosis composition to a second target area.

According to one or more embodiments of the present invention, there is also provided a method of using a hyperhidrosis kit wherein a subject in need applies a first hyperhidrosis composition to a first target area and then applies a second hyperhidrosis composition to a second target area daily.

According to one or more embodiments of the present invention, there is also provided a method of using a hyperhidrosis kit wherein a subject in need applies a first hyperhidrosis composition to a first target area and then applies a second hyperhidrosis composition to a second target area daily for a period of at least two weeks.

According to one or more embodiments of the present invention, there is also provided a method of using a hyperhidrosis kit to identify which platform composition is more suitable for a subject in need wherein the subject in need applies a first hyperhidrosis composition to a first parallel or substantially equivalent target area and then applies a second hyperhidrosis composition to a second or substantially equivalent parallel target area and then observes at which target area the level of hyperhidrosis is apparently less.

According to one or more embodiments of the present invention, there is also provided a method of using a hyperhidrosis kit to identify which platform composition is more suitable for a subject in need wherein the subject in need applies daily a first hyperhidrosis composition to a first parallel or substantially equivalent target area and then applies daily a second hyperhidrosis composition to a second or substantially equivalent parallel target area and then observes at which target area the level of hyperhidrosis is apparently less.

According to one or more embodiments of the present invention, there is also provided a method of using a hyperhidrosis kit to identify which platform composition is more suitable for a subject in need wherein the subject in need applies daily for at least two weeks a first hyperhidrosis composition to a first parallel or substantially equivalent target area and then applies daily for at least two weeks a second hyperhidrosis composition to a second or substantially equivalent parallel target area and then observes at which target area the level of hyperhidrosis is apparently less.

In accordance with one or more embodiments of the present invention the hyperhidrosis topical composition further comprises an additional active agent.

In accordance with one or more embodiments of the present invention the additional active agent comprises a cosmetic active agent or a pharmaceutical active agent having a cosmetic or pharmaceutical effect other than or in addition to a hyperhidrosis ameliorating or reducing effect.

In accordance with one or more embodiments of the present invention there is also provided a hyperhidrosis topical composition wherein the hyperhidrosis composition also comprises a therapeutic agent having a therapeutic effect other than or in addition to a hyperhidrosis ameliorating or reducing effect.

According to one or more embodiments of the present invention, there is also provided a hyperhidrosis kit comprising at least a first hyperhidrosis composition in an aerosol container accommodating a pressurized product and having an outlet capable of releasing the pressurized product as a foam and at least a second hyperhidrosis composition in an aerosol container accommodating a pressurized product and having an outlet capable of releasing the pressurized product as a foam wherein the first composition is selected from the group consisting of an oil in water emulsion; a water in oil emulsion; a petrolatum in aqueous emulsion; a petrolatum waterless formulation; a waterless oleaginous formulation; and a waterless polyethylene glycol or a waterless propylene glycol based composition, said first composition comprising a first active agent, suitable for the treatment or prevention of hyperhidrosis wherein the second composition is selected from the group consisting of an oil in water emulsion; a water in oil emulsion; a petrolatum in aqueous emulsion; a petrolatum waterless formulation; a waterless oleaginous formulation; and a waterless polyethylene glycol or a waterless propylene glycol based composition, said second composition comprising a second active agent, other than or in addition to a hyperhidrosis ameliorating or reducing agent.

Thus, according to one or more embodiments of the present invention, the foamable platform composition, includes:
  a. a foamable platform carrier;
  b. at least one hyperhidrosis agent or mixtures thereof;
  c. optionally a second active agent which can provide support to the hyperhidrosis effect; and
  d. a propellant at a concentration of about 3% to about 45% by weight of the total composition, wherein the composition is stored in an aerosol container and upon release expands to form a foam.

In accordance with one or more embodiments of the present invention, the foamable platform composition further comprises at least one component, selected from the group consisting of:

i. a surfactant;
ii. co-emulsifier or foam stabilizer;
iii. a polymeric agent;
iv. a viscosity, bulking or firming agent;
v. a stabilizer;
vi. a foam adjuvant;
vii. a co-solvent;
viii. a penetration enhancer;
ix. an agent capable of having an occlusive effect; and
x. a modulating agent.

In accordance with one or more embodiments of the present invention the foamable platform emollient emulsion carrier composition comprises:
 a. an aqueous carrier;
 b. an emollient; and
 c. a surfactant; or polymeric agent; and optionally
 d. one or more agents selected from the group consisting of a co-emulsifier and foam stabilizer; a viscosity, bulking or firming agent; a stabilizer; a co-solvent; a penetration enhancer; a foam adjuvant; a modulating agent and or an agent capable of having an occlusive effect, wherein the presence of an aluminum salt or other hyperhidrosis agent in a composition does not prevent a foam of good or satisfactory quality from being produced and wherein the composition is stored in an aerosol container and upon release expands to form a breakable foam.

In accordance with one or more embodiments of the present invention the foamable platform waterless carrier composition comprises:
 a. a non-aqueous carrier;
 b. a surfactant; and or a polymeric agent and optionally
 c. one or more agents selected from the group consisting of a co-emulsifier, foam stabilizer; a viscosity, bulking or firming agent, a modulating agent and or an agent capable of having an occlusive effect
wherein the presence of significant amounts of an aluminum salt or other hyperhidrosis agent in a composition does not prevent a foam of good or satisfactory quality from being produced and wherein the composition is stored in an aerosol container and upon release expands to form a breakable foam.

In accordance with one or more embodiments of the present invention the propellant is itself a cooling agent and may in large amounts produce a cooling sensation on the area of application and possibly thereby having a temporary affect on hyperhidrosis, such as transitionally ameliorating the amount of perspiration.

In accordance with one or more embodiments of the present invention there is provided a foamable platform composition for use with a hyperhidrosis agent comprising:
 a. a foamable platform carrier; and
 b. a propellant at a concentration of about 3% to about 45% by weight of the total composition,
wherein the composition is stored in an aerosol container and upon release expands to form a foam.

In accordance with one or more further embodiments of the present invention the propellant is at a concentration from about 3% to about 25% by weight of the total composition.

In accordance with one or more embodiments of the present invention the foamable composition is flowable or substantially flowable.

In accordance with one or more embodiments of the present invention the hyperhidrosis topical composition further comprises an additional active agent.

In accordance with one or more embodiments of the present invention the flowable carrier composition, comprises at least one carrier, selected from the group consisting of water, an oil, a silicone oil, an alcohol, a polyol, a polyethylene glycol (PEG), a propylene glycol, and a solvent or combinations thereof.

In accordance with one or more embodiments of the present invention the flowable composition, comprises at least one carrier, which is an aqueous carrier.

In accordance with one or more embodiments of the present invention the flowable composition, comprises at least one carrier, which is a non-aqueous carrier.

In certain embodiments of the present invention the carrier is an aqueous carrier.

In certain embodiments of the present invention the carrier is a non-aqueous or substantially non-aqueous carrier.

In certain embodiments of the present invention the carrier further contains a polar solvent.

In accordance with one or more embodiments of the present invention the main carrier solvent is at a concentration of about 40% to about 90% by weight of the total composition.

In accordance with one or more embodiments of the present invention the foamable composition further comprises at least one component, selected from the group consisting of:
 a surface active agent; and
 a polymeric agent,
wherein the presence of an aluminum salt or other hyperhidrosis agent in a composition does not prevent a foam of good or satisfactory quality from being produced and wherein the composition is stored in an aerosol container and upon release expands to form a breakable foam.

In accordance with one or more embodiments of the present invention the surface active agent is a stabilizing combination of at least two surface active agents.

In accordance with one or more embodiments of the present invention the surface active agent is at a concentration of about 0.1% to about 10% by weight of the total composition.

In accordance with one or more embodiments of the present invention the polymeric agent is at a concentration of about 0.05% to about 5% by weight of the total composition.

In accordance with one or more embodiments of the present invention the surface active agent is combination of at least two surfactants.

In accordance with one or more embodiments of the present invention where the composition is an emollient emulsion the polymeric agent is preferably a combination of hydroxy propylmethyl cellulose and xantham gum. In certain other embodiments the polymeric agent is sodium carboxymethyl-cellulose, hydroxyethyl-cellulose, microcrystalline-cellulose, aluminum starch octyl succinate, and polyacrylates such as carbopol.

In accordance with one or more embodiments of the present invention where the composition is an emollient emulsion the polymeric agent is preferably a hydroxypropyl-cellulose such as Klucel EF, aluminum starch octyl succinate, and polyacrylates such as carbopol.

In accordance with one or more embodiments of the present invention the co-emulsifier is at a concentration of about 0.05% to about 10% by weight of the total composition.

In accordance with one or more embodiments of the present invention the viscosity, bulking or firming agent is at a concentration of about 0.1% to about 15% by weight of the total composition.

In accordance with one or more embodiments of the present invention the stabilizer is at a concentration of about 0.1% to about 10% by weight of the total composition.

In accordance with one or more embodiments of the present invention the co-solvent is at a concentration of about 0.1% to about 48% by weight of the total composition, preferably about 0.1% to about 30% by weight of the total composition.

In accordance with one or more embodiments of the present invention the penetration enhancer is at a concentration of about 0.1% to about 30% by weight of the total composition.

In accordance with one or more embodiments of the present invention the agent capable of having an occlusive effect is at a concentration of about 45% to about 85% by weight of the total composition.

In accordance with one or more other embodiments of the present invention the agent capable of having an occlusive effect is at a concentration of about 25% to about 49% by weight of the total composition.

In accordance with one or more embodiments of the present invention the agent capable of having an occlusive effect is at a concentration of about less than 10% to about 30% by weight of the total composition.

In accordance with one or more embodiments of the present invention there is also provided a hyperhidrosis topical composition wherein the resultant foam has a density of about 0.01 to about 0.2 g/ml.

In accordance with one or more embodiments of the present invention there is also provided a hyperhidrosis topical composition wherein the resultant foam is a breakable foam, which if not subjected to mechanical shear break, is capable of remaining substantially intact without substantial foam collapse for about 50 seconds or more.

In accordance with one or more embodiments of the present invention there is also provided a hyperhidrosis topical composition wherein the resultant foam is a breakable foam, which if not subjected to mechanical shear break, is capable of remaining substantially intact without substantial foam collapse for about 120 seconds or more.

In accordance with one or more embodiments of the present invention there is also provided a hyperhidrosis topical composition wherein the resultant foam is a breakable foam, which if not subjected to mechanical shear break, is capable of remaining substantially intact without substantial foam collapse for about 300 seconds or more.

In an exemplary embodiment, the foamable hyperhidrosis composition is an aqueous composition, containing water and further comprises a surface active agent.

In an exemplary embodiment, the foamable hyperhidrosis topical composition comprises an aliphatic alcohol, water, a fatty alcohol and a surface active agent.

In an exemplary embodiment, the foamable hyperhidrosis topical composition is an emulsion, comprising water, a hydrophobic solvent, a surface-active agent and a polymeric agent.

Optionally, in one or more embodiments the emulsion-type foamable composition further contains a foam adjuvant agent, selected from the group consisting of a fatty alcohol having 15 or more carbons in their carbon chain; a fatty acid having 16 or more carbons in their carbon chain.

In certain embodiments, the emulsion is an oil in water emulsion, while in additional embodiments the emulsion is a water in oil emulsion.

In certain embodiments the hydrophobic carrier is an oil. Exemplary oils include mineral oil, silicone oil, a triglyceride and an ester of a fatty acid. In certain embodiments, the hydrophobic solvent is occlusive, such as petrolatum, while in other embodiments the hydrophobic carrier in non-occlusive.

In an exemplary embodiment, the foamable hyperhidrosis topical composition is an oleaginous foamable composition, including at least one solvent selected from a hydrophobic solvent, a silicone oil, an emollient, a polar solvent and mixtures thereof, wherein the solvent is present at a concentration of about 70% to about 96.5% by weight of the total composition, at least a non-ionic surface-active agent and at least one polymeric agent.

In an exemplary embodiment, the foamable hyperhidrosis topical composition includes more than 50% of a polar solvent (as used herein, the term "polar solvent" shall mean a material that produces a uniform, clear or hazy, mixture when combined with at least a weight equivalent of water), a surface-active agent and a polymeric agent.

In certain embodiments the foamable composition contains up to 80% water, while in additional embodiments the foamable composition contains up to 25% water.

In one or more embodiments, the composition is substantially alcohol free

In one or more embodiments, the composition is substantially non-aqueous.

In accordance with one or more embodiments of the present invention there is provided a method of treating, alleviating or preventing a dermatological reaction, sensation or disorder of a mammalian subject, comprising:
  a. administering an effective amount of a hyperhidrosis topical emollient emulsion carrier composition to a target site on a mammalian subject, comprising:
    i. an aqueous carrier at a concentration of about 40% to about 90% by weight of the total composition;
    ii. an emollient at a concentration of about 5% to about 15% by weight of the total composition;
    iii. a surfactant at a concentration of about 0.1% to about 10% by weight of the total composition;
    iv. a polymeric agent at a concentration of about 0.1% to about 5% by weight of the total composition;
    v. a propellant at a concentration of about 3% to about 45% by weight of the total composition
    vi. at least one active agent in an effective amount which is intended to prevent, alleviate or treat hyperhidrosis; and optionally
    vii. a co-emulsifier and foam stabilizer at a concentration of about 0.1% to about 5% by weight of the total composition; a viscosity, bulking or firming agent at a concentration of about 0.1% to about 15% by weight of the total composition; a stabilizer; a co-solvent at a concentration of about 0.1% to about 20% by weight of the total composition; a penetration enhancer at a concentration of about 0.1% to about 20% by weight of the total composition; a modulating agent and or an agent capable of having an occlusive effect at a concentration of about 5% to about 30% by weight of the total composition;
  wherein the presence of significant amounts of an aluminum salt or other hyperhidrosis agent in a composition does not prevent a foam of good or satisfactory quality from being produced and wherein the composition is stored in an aerosol container and upon release expands to form a breakable foam, and
  b. applying mechanical shear break to the applied foam such that it is spread at, about and within the target site.

In accordance with one or more embodiments of the present invention there is provided a method of treating, alleviating or preventing a dermatological reaction, sensation or disorder of a mammalian subject, comprising:

a. administering an effective amount of a hyperhidrosis topical substantially waterless or waterless foamable composition to a target site on a mammalian subject, comprising:
   i. a non-aqueous carrier at a concentration of about 40% to about 90% by weight of the total composition;
   ii. a surfactant at a concentration of about 0.1% to about 10% by weight of the total composition; and or a polymeric agent at a concentration of about 0.1% to about 5% by weight of the total composition;
   iii. at least one active agent in an effective amount which is intended to prevent, alleviate, treat hyperhidrosis;
   iv. a propellant at a concentration of about 3% to about 25% by weight of the total composition and optionally;
   v. a co-emulsifier and foam stabilizer at a concentration of about 0.1% to about 5% by weight of the total composition; and a viscosity, bulking or firming agent at a concentration of about 0.1% to about 15% by weight of the total composition, wherein the presence of significant amounts of an aluminum salt or other hyperhidrosis agent in a composition does not prevent a foam of good or satisfactory quality from being produced and wherein the composition is stored in an aerosol container and upon release expands to form a breakable foam; and b. applying mechanical shear break to the applied foam such that it is spread at, about and within the target site.

In one or more embodiments there is provided an organic carrier platform selected from the group consisting of a hydrophobic organic carrier, a polar solvent, an emollient and any mixture thereof, at a concentration of about 2% to about 50% by weight;
   (3) about 0.1% to about 5% by weight of a surface-active agent;
   (4) about 0.01% to about 5% by weight of at least one polymeric agent selected from the group consisting of a bioadhesive agent, a gelling agent, a film forming agent and a phase change agent; and
   (5) a liquefied or compressed gas propellant at a concentration of about 3% to about 25% by weight of the total composition.

According to still further embodiments of the present invention, the foamable composition further includes about 0.1% to about 5% by weight of a foam adjuvant is selected from the group consisting of a fatty alcohol having 15 or more carbons in their carbon chain; a fatty acid having 16 or more carbons in their carbon chain; a fatty alcohol, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid and any mixture thereof.

In one or more embodiments of the present invention the carrier or composition comprises a single phase.

In one or more embodiments of the present invention the carrier or composition is non aqueous and comprises a single phase.

In one or more embodiments of the present invention the carrier or composition comprises an emulsion.

In one or more embodiments of the present invention the carrier or composition comprises an oil in water emulsion.

In one or more embodiments of the present invention the carrier or composition comprises a water in oil emulsion.

In one or more embodiments of the present invention the carrier or composition comprises a waterless oleaginous emulsion.

In one or more embodiments of the present invention the carrier or composition comprises a waterless polyethylene glycol based formulation.

In one or more embodiments of the present invention the carrier or composition comprises a waterless propylene glycol based formulation.

In one or more embodiments of the present invention the carrier or composition comprises a petrolatum in solvent emulsion.

In one or more embodiments of the present invention the carrier or composition comprises a solvent in petrolatum emulsion wherein the solvent is selected from water or a non aqueous solvent In one or more embodiments of the present invention the carrier or composition comprises water in petrolatum emulsion.

In one or more embodiments of the present invention the carrier or composition comprises a unique solvent in petrolatum emulsion wherein the solvent is a non aqueous solvent.

In one or more embodiments of the present invention the carrier or composition comprises a unique hydrophilic solvent in petrolatum emulsion.

For the non waterless carriers and compositions water and optional ingredients are added to complete the total mass to 100%. For the waterless carriers and compositions a non aqueous solvent and optional ingredients are added to complete the total mass of 100%. In certain embodiments the propellant is added to the total mass. Upon release from an aerosol container, the foamable composition forms an expanded foam suitable for topical administration. The expanded mass will correspond to or reflect the formulation prior to the addition of propellant According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

The active agent, suitable for the treatment or prevention of hyperhidrosis, is selected from the group consisting of an anticholinergic drug, a boric acid, a tannic acid, a resorcinol, a potassium permanganate, a formaldehyde, a glutaraldehyde and a methenamine. In one or more embodiments the agents for the treatment of hyperhidrosis is a Lewis acid. Typically, the Lewis acid is a partially neutralized salt of metal ions such as aluminum and zirconium. Exemplary metal ion salts, suitable to reduce hyperhidrosis are aluminum salts, and aluminum zirconium complexes, non limiting examples are aluminum chloride; aluminium sesquichlorohydrate; aluminum and/or zirconium chlorohydrates; aluminum-zirconium-Glycine (AZG) complexes; and aluminum hydroxybromide, which are typical included in antiperspirant preparations. The aluminum ions act by penetrating into eccrine-gland ducts at the opening of the epidermis. When the aluminum ions are drawn into the cells, water passes in with them. As more water flows in, the cells begin to swell, squeezing the ducts closed so that sweat cannot get out. In one or more embodiments, the agents for the treatment of hyperhidrosis is a glycopyrrolate compound. In one or more embodiments, the agents for the treatment of hyperhidrosis is a 5-alpha-reductase inhibitor. Examples of 5-alpha-reductase inhibitors include, but are not limited to finasteride, epristeride, flutamide, spironolactone, saw palmetto extract, and cholestan-3-one. In one or more embodiments, the agents for the treatment of hyperhidrosis is selected from the group consisting of a mono- and dicarboxylic acid having 4 to 18 carbon atoms, a mercapto derivative thereof, a salts thereof, and an ester thereof. In one or more embodiments, the agents for the treatment of hyperhidrosis is botulinum toxin. In one or more embodiments, the agents for the treatment of hyperhidrosis consists of a 5-HT2C receptor antagonist. Examples of 5-HT2C receptor antagonist include, but are not limited to ketanserin, ritanserin, mianserin, mesulergine, cyproheptadine, fluoxetine, mirtazapine, olanzapine, and ziprasidone. Yet, another class of agents for the treatment of hyperhidrosis includes 5-HT2C receptor modulators (i.e., inverse agonists, partial agonists, and allosteric modulators).

In one or more other embodiments the active agent, suitable for the treatment or prevention of hyperhidrosis, is selected from the group consisting of diphemanil metisulfate, aluminum chlorohydrate, aluminum hydroxybromide, aluminum chloride, ASOS; aluminum sulfate, aluminum zirconium complexes such as aluminium zirconium tetrachlorohydrex glycerine, propantheline, glycopyrrolate, benzotropine, oxybutynin, gluteraldehyde, azelaic acid, aluminum zirconium tetrachlorohydrex, aluminum chlorohydrex polyethylene glycol, hyoscine hydrobromide.

In one or more other embodiments the active agent, suitable for the treatment or prevention of hyperhidrosis, is a combination of two or more active agents. For example an aluminum or zirconium salt plus an anti-cholinergic agent; an aluminum or zirconium salt plus a glycopyrrolate; an aluminum or zirconium salt plus an anti-inflammatory or anti-pyretic such as acetylsalicylic acid, paracetemol, piroxicam, naproxen, diclofenac and the like; an aluminum or zirconium salt plus a vasoconstrictor such as clonidine; an aluminum or zirconium salt plus a benzodiazepine.

In one or more other embodiments the active agent, suitable for the treatment or prevention of hyperhidrosis, is an aluminum salt selected from the group consisting of aluminum chloride; aluminum chlorohydrate; aluminum chlorohydrex polyethylene glycol aluminum chlorohydrex; complex polyethylene glycol; aluminum chlorohydrex propylene glycol aluminum chlorohydrex; complex. propylene glycol; aluminum dichlorohydrate; aluminum dichlorohydrex polyethylene aluminum dichlorohydrex; glycol complex polyethylene glycol; aluminum dichlorohydrex propylene glycol aluminum dichlorohydrex; complex. propylene glycol; aluminum sesquichlorohydrate; aluminum sesquichlorohydrex polyethylene aluminum sesquichloro-hydrex; glycol complex polyethylene glycol; aluminum sesquichlorohydrex propylene aluminum sesquichloro-hydrex; glycol complex propylene glycol; aluminum sulfate buffered; aluminum zirconium octachlorohydrate; aluminum zirconium octachlorohydrex aluminum zirconium; glycine complex octachlorohydrex gly; aluminum zirconium pentachlorohydrate; aluminum zirconium pentachlorohydrex aluminum zirconium; glycine complex pentachlorohydrex gly; aluminum zirconium tetrachlorohydrate aluminum zirconium tetrachlorohydrex aluminum zirconium; glycine complex tetrachlorohydrex gly; aluminum zirconium trichlorohydrate; aluminum zirconium trichlorohydrex glycine aluminum zirconium; complex trichlorohydrex gly; aluminum sulfate buffered with sodium aluminum lactate.

The foamable composition of the present invention can be an emulsion, or microemulsion, including an aqueous phase and an organic carrier phase. The organic carrier is selected from the group consisting of a hydrophobic organic carrier (also termed herein "hydrophobic solvent"), an emollient, a polar solvent, and any mixture thereof. The identification of a organic carrier or "solvent", as used herein, is not intended to characterize the solubilization capabilities of the solvent for any specific active agent or any other component of the foamable composition. Rather, such information is provided to aid in the identification of materials suitable for use as an organic carrier in the foamable compositions described herein.

A "hydrophobic organic carrier" as used herein refers to a material having solubility in distilled water at ambient temperature of less than about 1 gm per 100 mL, more preferable less than about 0.5 gm per 100 mL, and most preferably less than about 0.1 gm per 100 mL. It is liquid at ambient temperature.

In one or more embodiments, the hydrophobic organic carrier is an oil, such as mineral oil. According to one or more embodiments, hydrophobic solvents are liquid oils originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or any mixture thereof, in any proportion.

Suitable hydrophobic solvents also include polyunsaturated oils containing poly-unsaturated fatty acids. In one or more embodiments, the unsaturated fatty acids are selected from the group consisting of an omega-3 fatty acid and a omega-6 fatty acid. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which contribute to the therapeutic benefit of the present foamable composition. Thus, the hydrophobic solvent can include at least 6% of an oil selected from the group consisting of an omega-3 oil, an omega-6 oil, and any mixture thereof. In the context of the present invention, oils that possess therapeutically-beneficial properties are termed "therapeutically active oil".

Another class of hydrophobic solvents is the essential oils, which are also considered therapeutically active oil, which contain active biologically occurring molecules and, upon topical application, exert a therapeutic effect, which is conceivably synergistic to the beneficial effect of the NSAID in the composition.

Another class of therapeutically active oils includes liquid hydrophobic plant-derived oils, which are known to possess therapeutic benefits when applied topically.

Silicone oils also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. These are chosen from cyclic or linear polydimethylsiloxanes containing from about 3 to about 9. Volatile silicones such as cyclomethicones can also be used. Silicone oils are also considered therapeutically active oil, due to their barrier retaining and protective properties.

In one or more embodiments, the hydrophobic carrier includes at least 2% by weight silicone oil or at least 5% by weight.

The solvent may be a mixture of two or more of the above hydrophobic solvents in any proportion.

A further class of solvents includes "emollients" that have a softening or soothing effect, especially when applied to body areas, such as the skin and mucosal surfaces. Emollients are not necessarily hydrophobic. Examples of suitable emollients include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and any mixture thereof.

According to one or more embodiments of the present invention, the hydrophobic organic carrier includes a mixture of a hydrophobic solvent and an emollient. According to one or more embodiments, the foamable composition is a mixture of mineral oil and an emollient in a ratio between 2:8 and 8:2 on a weight basis.

A "polar solvent" is an organic solvent, typically soluble in both water and oil. Examples of polar solvents include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, sulfoxides, such as dimethylsulfoxide (DMSO), dimethylformanide, methyl dodecyl sulfoxide, dimethylacetamide, dimethylisosorbide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the polar solvent is a polyethylene glycol (PEG) or PEG derivative that is liquid at ambient temperature.

A non-limiting exemplary list of solvents that can be considered as potent solvents includes polyethylene glycol, propylene glycol, hexylene glycol, butaneediols and isomers thereof, glycerol, benzyl alcohol, DMSO, ethyl oleate, ethyl caprylate, diisopropyl adipate, dimethylacetamide, N-methylpyrrolidone, N-hydroxyethylpyrrolidone, polyvinylpyrrolidone, isosorbide derivatives, such as dimethyl isosorbide, glycofurol and ethoxydiglycol (transcutol) and laurocapram.

In one or more embodiments of the present invention non limiting examples of non aqueous solvent are solvents such as polyethylene glycol (PEG), isosorbide derivatives, such as dimethyl isosorbide, propylene glycol (PG), hexylene glycol and glycerin, diethylene glycol monoethyl ether, a liquid polyethylene glycol, glycofurol, tetrahydrofurfuryl alcohol, polyethyleneglycol, ether, DMSO, a pyrrolidone, N-methyl pyrrolidones, N-Methyl-2-pyrrolidone, 1-Methyl-2-pyrrolidinone, ethyl proxitol, dimethylacetamide, a PEG-type surfactant, an alpha hydroxy acid, lactic acid and glycolic acid, hexylene glycol, benzyl alcohol, DMSO, glycofurol and ethoxydiglycol (transcutol), butylene glycols, glycerol, pentaerythritol, sorbitol, mannitol, oligosaccharides, monooleate of ethoxylated glycerides having about 8 to 10 ethylene oxide units, and cyclodextrins, esters, such as ethyl propionate, tributylcitrate, acetyl triethylcitrate, acetyl tributyl citrate, triethylcitrate, ethyl butyrate, propylene glycol monoacetate, propylene glycol diacetate, .epsilon.-caprolactone and isomers thereof, .delta.-valerolactone and isomers thereof, beta.-butyrolactone and isomers thereof; and other solubilizers known in the art, such as dimethyl acetamide.

In an embodiment of the present invention the non aqueous solvent is monooctanoin.

In one or more embodiments of the present invention the carrier or composition comprises a unique hydrophillic solvent with petrolatum emulsion, wherein preferably the hydrophilic solvent is selected from a liquid polyethylene glycol, a propylene glycol or dimethyl isosorbide.

In one or more embodiments of the present invention the carrier or composition comprises a solvent wherein the solvent is a penetration enhancer or helps to solubilise to some extent an active agent.

The polymeric agent serves to stabilize the foam composition and to control drug residence in the target organ. Exemplary polymeric agents, are classified below in a non-limiting manner. In certain cases, a given polymer can belong to more than one of the classes provided below.

In one or more embodiments, the polymeric agent is a gelling agent. A gelling agent controls the residence of a therapeutic composition in the target site of treatment by increasing the viscosity of the composition, thereby limiting the rate of its clearance from the site. Many gelling agents are known in the art to possess mucoadhesive properties.

The gelling agent can be a natural gelling agent, a synthetic gelling agent and an inorganic gelling agent. Exemplary gelling agents that can be used in accordance with one or more embodiments of the present invention include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are contemplated.

Further exemplary gelling agents include the acrylic acid/ ethyl acrylate copolymers and the carboxyvinyl polymers sold, for example, by the B.F. Goodrich Company under the trademark of Carbopol® resins. These resins consist essentially of a colloidal water-soluble polyalkenyl polyether crosslinked polymer of acrylic acid crosslinked with from 0.75% to 2% of a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981. Carbopol® 934 is a water-soluble polymer of acrylic acid crosslinked with about 1% of a polyallyl ether of sucrose having an average of about 5.8 allyl groups for each sucrose molecule.

In one or more embodiment, the composition of the present invention includes at least one polymeric agent, which is a water-soluble cellulose ether. Preferably, the water-soluble cellulose ether is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose and carboxymethylhydroxyethylcellulose. More preferably, the water-soluble cellulose ether is selected from the group consisting of methylcellulose, hydroxypropyl cellulose and hydroxypropyl methylcellulose (Methocel). In one or more embodiments, the composition includes a combination of a water-soluble cellulose ether; and a naturally-occurring polymeric materials, selected from the group consisting of a xanthan gum, guar gum, carrageenan gum, locust bean gum and tragacanth gum.

Yet, in other embodiments, the gelling agent includes inorganic gelling agents, such as silicone dioxide (fumed silica).

Mucoadhesive/bioadhesion has been defined as the attachment of synthetic or biological macromolecules to a biological tissue. Mucoadhesive agents are a class of polymeric biomaterials that exhibit the basic characteristic of a hydrogel, i.e. swell by absorbing water and interacting by means of adhesion with the mucous that covers epithelia. Compositions of the present invention may contain a mucoadhesive macromolecule or polymer in an amount sufficient to confer bioadhesive properties. The bioadhesive macromolecule enhances the delivery of biologically active agents on or through the target surface. The mucoadhesive macromolecule may be selected from the group consisting of an acidic synthetic polymer, preferably including at least one acidic group per four repeating or monomeric subunit moieties, such as poly(acrylic)- and/or poly(methacrylic) acid (e.g., Carbopol®, Carbomer®), poly(methylvinyl ether/maleic anhydride) copolymer, a mixture thereof and copolymers copylmers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin. Such polymers may be present as free acids, bases, or salts, usually in a final concentration of about 0.01% to about 0.5% by weight.

A suitable bioadhesive macromolecule is the family of acrylic acid polymers and copolymers, (e.g., Carbopol®). These polymers contain the general structure—[CH$_2$—CH(COOH)—]$_n$. Hyaluronic acid and other biologically-derived polymers may be used.

Exemplary bioadhesive or mucoadhesive macromolecules have a molecular weight of at least 50 kDa, or at least 300 kDa, or at least 1,000 kDa. Favored polymeric ionizable macromolecules have not less than 2 mole percent acidic groups (e.g., COOH, SO$_3$H) or basic groups (NH$_2$, NRH, NR$_2$), relative to the number of monomeric units. The acidic or basic groups can constitute at least 5 mole percent, or at least 10 mole percent, or at least 25, at least 50 more percent, or even up to 100 mole percent relative to the number of monomeric units of the macromolecule.

Yet, another group of mucoadhesive agent includes inorganic gelling agents such as silicon dioxide (fumed silica), including but not limited to, AEROSIL 200 (DEGUSSA).

Many mucoadhesive agents are known in the art to also possess gelling properties.

The foam composition may contain a film forming component. The film forming component may include at least one water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as oleic and myristyl acid may be used in combination with the cellulose derivative.

In one or more embodiments, the composition of the present invention includes a phase change polymer, which alters the composition behavior from fluid-like prior to administration to solid-like upon contact with the target mucosal surface. Such phase change results from external stimuli, such as changes in temperature or pH and exposure to specific ions (e.g., Ca$^{2+}$).

Non-limiting examples of phase change polymers include poly(N-isopropylamide) and Poloxamer 407®.

The polymeric agent is present in an amount in the range of about 0.01% to about 5.0% by weight of the foam composition. In one or more embodiments, it is typically less than about 1 wt % of the foamable composition.

Surface-Active Emulsifier or Surface-Active Agent

The composition of the present invention further contains an emulsifier a surface-active agent or surfactant and such terms can be used interchangeably. Surface-active agents (also termed "surfactants") include any agent linking oil and water in the composition, in the form of emulsion. A surfactant's hydrophilic/lipophilic balance (HLB) describes the emulsifier's affinity toward water or oil. HLB is defined for non-ionic surfactants. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average). In many cases a single surfactant may suffice. In other cases a combination of two or more surfactants is desired. As will be appreciated by a person skilled in the art which surfactant or surfactant system is more appropriate is related to the vehicle and intended purpose. In general terms a combination of surfactants is usually preferable where the vehicle is an emulsion. In a waterless or substantially waterless environment it has been discovered that the presence of a surfactant or combination of surfactants can be significant in producing breakable forms of good quality.

The generally thought considerations for oil in water emulsions of using a surfactant or surfactant combination with preferably a HLB value or average in or towards the lipophilic side of the scale may not be applicable for silicone comprising waterless or substantially waterless systems as described herein.

According to one or more embodiments the composition contains a single surface active agent having an HLB value between about 2 and 9, or more than one surface active agent and the weighted average of their HLB values is between about 2 and about 9.

According to one or more embodiments the composition contains a single surface active agent having an HLB value between about 7 and 14, or more than one surface active agent and the weighted average of their HLB values is between about 7 and about 14.

According to one or more other embodiments the composition contains a single surface active agent having an HLB value between about 9 and about 19, or more than one surface active agent and the weighted average of their HLB values is between about 9 and about 19.

Preferably, the composition of the present invention contains a non-ionic surfactant. Non-limiting examples of possible non-ionic surfactants include a polysorbate, polyoxyethylene (20) sorbitan monostearate, polyoxyethylene (20) sorbitan monooleate, a polyoxyethylene fatty acid ester, Myrj 45, Myrj 49, Myrj 52 and Myrj 59; a polyoxyethylene alkyl ether, polyoxyethylene cetyl ether, polyoxyethylene palmityl ether, polyethylene oxide hexadecyl ether, polyethylene glycol cetyl ether, brij 38, brij 52, brij 56 and brij W1, a sucrose ester, a partial ester of sorbitol and its anhydrides, sorbitan monolaurate, sorbitan monolaurate a monoglyceride, a diglyceride, isoceteth-20 and mono-, di- and tri-esters of sucrose with fatty acids.

Non-limiting examples of non-ionic surfactants that have HLB of about 7 to about 12 include steareth 2 (HLB~4.9); glyceryl monostearate/PEG 100 stearate (Av HLB~11.2); stearate Laureth 4 (HLB~9.7) and cetomacrogol ether (e.g., polyethylene glycol 1000 monocetyl ether). Exemplary stabilizing surfactants which may be suitable for use in the present invention are found below.

PEG-Fatty Acid Monoester Surfactants

| Chemical name | Product example name | HLB |
|---|---|---|
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-45 stearate | Nikkol MYS-45 (Nikko) | 18 |
| PEG-50 stearate | Myrj 53 | >10 |
| PEG-100 stearate | Myrj 59, Arlacel 165 (ICI) | 19 |

PEG-Fatty Acid Diester Surfactants:

| Chemical name | Product example name | HLB |
|---|---|---|
| PEG-4 dilaurate | Mapeg 200 DL (PPG), Kessco PEG 200 DL (Stepan), LIPOPEG 2-DL (Lipo Chem.) | 7 |
| PEG-4 | distearate Kessco 200 DS (Stepan) | 5 |
| PEG-32 dioleate | Kessco PEG 1540 DO (Stepan) | 15 |
| PEG-400 dioleate) | Cithrol 4DO series (Croda) | >10 |
| PEG-400 disterate | Cithrol 4DS series (Croda) | >10 |
| PEG-20 glyceryl oleate | Tagat O (Goldschmidt) | >10 |

Transesterification Products of Oils and Alcohols

| Chemical name | Product example name | HLB |
|---|---|---|
| PEG-30 castor oil | Emalex C-30 (Nihon Emulsion) | 11 |
| PEG-40 hydrogenated castor oil) | Cremophor RH 40 (BASF), Croduret (Croda), Emulgin HRE 40 (Henkel) | 13 |
| Polyglyceryl-6 dioleate | Caprol 6G20 (ABITEC); PGO-62 (Calgene), PLUROL OLEIQUE CC 497 (Gattefosse)Hodag | 8.5 |

PEG-Sorbitan Fatty Acid Esters

| Chemical name | Product example name | HLB |
|---|---|---|
| PEG-20 sorbitan monopalmitate | Tween 40 (Atlas/ICI), Crillet 2 (Croda) | 16 |
| PEG-20 sorbitan monostearate | Tween-60 (Atlas/ICI), Crillet 3 (Croda) | 15 |
| PEG-20 sorbitan | Tween-80 (Atlas/ICI), Crillet 4 (Croda) | 15 |
| PEG-20 sorbitan | Tween-80 (Atlas/ICI), Crillet 4 (Croda) | 15 |

Polyethylene Glycol Alkyl Ethers

| Chemical name | Product example name | HLB |
|---|---|---|
| PEG-2 oleyl ether | oleth-2 Brij 92/93 (Atlas/ICI) | 4.9 |
| PEG-3 oleyl ether | oleth-3 Volpo 3 (Croda) | <10 |
| PEG-5 oleyl ether | oleth-5 Volpo 5 (Croda) | <10 |
| PEG-10 oleyl ether | oleth-10 Volpo 10 (Croda), Brij 96/97 (Atlas/ICI) | 12 |
| PEG-20 oleyl ether | oleth-20 Volpo 20 (Croda), Brij 98/99 (Atlas/ICI) | 15 |
| PEG-4 lauryl ether | laureth-4Brij 30 (Atlas/ICI) | 9.7 |
| PEG-23 lauryl ether | laureth-23Brij 35 (Atlas/ICI) | 17 |
| PEG-10 stearyl ether | Brij 76 (ICI) | 12 |
| PEG-2 cetyl ether | Brij 52 (ICI) | 5.3 |

Sugar Ester Surfactants

| Chemical name | Product example name | HLB |
|---|---|---|
| Sucrose distearate | Sisterna SP50, Surfope 1811 | 11 |

Sorbitan Fatty Acid Ester Surfactants

| Chemical name | Product example name | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |

In one or more embodiments the surface active agent is a complex emulgator in which the combination of two or more surface active agents can be more effective than a single surfactant and provides a more stable emulsion or improved foam quality than a single surfactant. For example and by way of non-limiting explanation it has been found that by choosing say two surfactants, one hydrophobic and the other hydrophilic the combination can produce a more stable emulsion than a single surfactant. Preferably, the complex emulgator comprises a combination of surfactants wherein there is a difference of about 4 or more units between the HLB values of the two surfactants or there is a significant difference in the chemical nature or structure of the two or more surfactants.

Specific non limiting examples of surfactant systems are, combinations of polyoxyethylene alkyl ethers, such as Brij 59/Brij10; Brij 52/Brij 10; Steareth 2/Steareth 20; Steareth 2/Steareth 21 (Brij 72/Brij 721); combinations of polyoxyethylene stearates such as Myrj 52/Myrj 59; combinations of sucrose esters, such as Surphope 1816/Surphope 1807; combinations of sorbitan esters, such as Span 20/Span 80; Span 20/Span 60; combinations of sucrose esters and sorbitan esters, such as Surphope 1811 and Span 60; combinations of liquid polysorbate detergents and PEG compounds, such as Tween 80/PEG-40 stearate; methyl glucose sesquistearate; polymeric emulsifiers, such as Permulen (TR1 or TR2); liquid crystal systems, such as Arlatone (2121), Stepan (Mild RM1), Nikomulese (41) and Montanov (68) and the like.

In certain embodiments the surfactant is preferably a combination of steareth-2 and steareth-21; in certain other embodiments the surfactant is a combination of polysorbate 80 and PEG-40 stearate. In certain other embodiments the surfactant is a combination of glyceryl monostearate/PEG 100 stearate. In certain other embodiments the surfactants is a combination of steareth 2 and methyl glucose sesquistearate. In certain other embodiments the surfactants is a combination of steareth 2 and cetearyl alcohol and cetearyl glucoside.

In certain cases, the surface active agent is selected from the group of cationic, zwitterionic, amphoteric and ampholytic surfactants, such as sodium methyl cocoyl taurate, sodium methyl oleoyl taurate, sodium lauryl sulfate, triethanolamine lauryl sulfate and betaines.

Many amphiphilic molecules can show lyotropic liquid-crystalline phase sequences depending on the volume balances between the hydrophilic part and hydrophobic part. These structures are formed through the micro-phase segregation of two incompatible components on a nanometer scale. Soap is an everyday example of a lyotropic liquid crystal. Certain types of surfactants tend to form lyotropic liquid crystals in emulsions interface (oil-in-water) and exert a stabilizing effect. Non limiting examples of surfactants with postulated tendency to form interfacial liquid crystals are: phospholipids, alkyl glucosides, sucrose esters, sorbitan esters. In certain embodiments of the present invention surfactants which tend to form liquid crystals may improve the quality of foams produced from compositions of the present invention.

In one or more embodiments the carrier or composition is capable of forming or tends to form liquid crystals.

In one or more embodiments the carrier or composition, comprises liquid crystals.

In one or more embodiments the carrier or composition, comprises liquid crystals wherein the liquid crystals are relatively few.

In one or more embodiments the at least one surface active agent is solid, semi solid or waxy;

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide formulations and foams of good or excellent quality in the waterless and substantially waterless carriers and compositions of the present invention.

Thus, in a preferred embodiment, the surface active agent, the composition contains a non-ionic surfactant. In another preferred embodiment the composition includes a mixture of non-ionic surfactants as the sole surface active agent. Yet, in additional embodiments, the foamable composition includes a mixture of at least one non-ionic surfactant and at least one ionic surfactant in a ratio in the range of about 100:1 to 6:1. In further embodiments, surface active agent comprises a combination of a non-ionic surfactant and an ionic surfactant, at a ratio of between 1:1 and 20:1.

In selecting a suitable surfactant or combination thereof it should be borne in mind that the upper amount of surfactant that may be used may be limited by the shakability of the composition. In general terms, as the amount of non liquid surfactant is increased the shakability of the formulation reduces until a limitation point is reached where the formulation becomes non shakable. Thus in an embodiment of the present invention any effective amount of surfactant may be used provided the formulation remains shakable or at least flowable. In the present invention where it is desirable to use a high molecular weight solvent and more particularly significant amounts it may be helpful to include a liquid surfactant in addition to or in place of a more waxy surfactant and or to increase the level of the surfactant.

In certain embodiments of the present invention the amount of surfactant or combination of surfactants is between about 0.05% to about 20%; between about 0.05% to about 15%. or between about 0.05% to about 10%.

Optionally, a foam adjuvant is included in the foamable compositions of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

In one or more embodiments, a combination of a fatty acid and a fatty ester is employed.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

An important property of the fatty alcohols and fatty acids used in context of the composition of the present invention is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and antiinflammatory properties (see, for example, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

Thus, in preferred embodiments of the present invention, a combined and enhanced therapeutic effect is attained by including both a nonsteroidal immunomodulating agent and a therapeutically effective foam adjuvant in the same composition, thus providing a simultaneous anti-inflammatory and antiinfective effect from both components. Furthermore, in a further preferred embodiment, the composition concurrently comprises an active agent, suitable for the treatment of hyperhidrosis and a therapeutically effective foam adjuvant and a therapeutically active oil, as detailed above. Such combination provides an even more enhanced therapeutic benefit. Thus, the foamable carrier, containing the foam adjuvant provides an extra therapeutic benefit in comparison with currently used vehicles, which are inert and non-active.

The foam adjuvant amount is about 0.1% to about 5% of the composition mass.

In one or more embodiments of the present invention, the solvent or secondary solvent is a polyol. A polyol is an organic substance that contains at least two hydroxy groups in its molecular structure.

In one or more embodiments, the foamable carrier contains at least one diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the foamable carrier contains at least one triol (a compound that contains three hydroxy groups in its molecular structure), such as glycerin, butane-1,2,3-triol, butane-1,2,4-triol and hexane-1,2,6-triol.

In one or more embodiments, the polyol is a mixture of polyols. In one or more embodiments, the mixture of polyols contains at least one diol and at least one triol. According to certain embodiments the ratio between the diol and triol is between 9:1 and 1:1.

In one or more embodiments, part of mixture of polyols is a saccharide. Exemplary saccharides include, but are not limited to monosaccharide, disaccharides, oligosaccharides and sugar alcohols.

A monosaccharide is a simple sugar that cannot be hydrolyzed to smaller units. Empirical formula is $(CH_2O)n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

A sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol.) Mixtures of polyols, including (1) at least one polyol selected from a diol and a triol; and (2) a In an embodiment of the present invention, the solvent consists of a polymerized ethylene glycol, namely polyethylene glycol, which is also termed "PEG." Exemplary PEGs are provided in the following table.

| Composition | Av. Molecular weight | Appearance | Melting point (° C.) |
|---|---|---|---|
| PEG 200 | 190~210 | Oily liquid | |
| PEG 300 | 285~315 | Oily liquid | |
| PEG 400 | 380~420 | Oily liquid | |
| PEG 600 | 570~630 | Oily liquid | 17~22 |
| PEG 1000 | 950~1050 | Solid | 35~40 |
| PEG 4000 | 3800~4400 | Solid | 53~58 |
| PEG 6000 | 5600~6400 | Solid | 55~60 |
| PEG 8000 | 7500~8500 | Solid | 58~65 |

Thus, in an embodiment of the present invention, the PEG is selected from the group consisting of PEG 200, PEG 300, PEG 400, PEG 600, PEG 1000, PEG 4000, PEG 6000 and PEG 8000. The foamable carrier according to the present invention can contain a single PEG or a mixture of two or more PEGs. PEGs having molecular weight of more that about 1000 possess gelling properties; i.e., they increase the viscosity of a composition. Therefore, by combining PEGs with different molecular weights/melting points, one can attain varying levels of flowability as desirable for the treatment of a given target site.

Petrolatum is known by various names including yellow soft paraffin, yellow petrolatum, mineral jelly; and petroleum jelly. Petrolatum is a purified mixture of semisolid saturated hydrocarbons having the general formula $C_nH_{2n+2}$, and is obtained from petroleum. The hydrocarbons consist mainly of branched and unbranched chains although some cyclic alkanes and aromatic molecules with paraffin side chains may also be present. Some forms may contain a suitable stabilizer (antioxidant). It is mainly used as an emollient and ointment base in topical pharmaceutical formulations creams and transdermal applications. Therapeutically, sterile gauze dressings containing petrolatum may be used for nonadherent wound dressings. Petrolatum is additionally widely used in cosmetics and in some food applications. It is odorless, and tasteless.

The rheological properties of petrolatum are determined by the ratio of the unbranched chains to the branched chains and cyclic components of the mixture. Petrolatum contains relatively high amounts of branched and cyclic hydrocarbons, in contrast to paraffin, which accounts for its softer character and makes it an ideal ointment base. In one or more embodiments of the present invention a petrolatum or a petrolatum mixture is selected such that it has a quality of relative softness.

Petrolatum is an inherently stable material. On exposure to light any impurities present may be Oxidation may be inhibited by the inclusion of a suitable antioxidant such as butylated hydroxyanisole, butylated hydroxytoluene, or alpha tocopherol.

In preparing petrolatum compositions they should not be heated for extended periods above the temperature necessary to achieve complete fluidity (approximately 75° C.).

Various grades of petrolatum are commercially available, which vary in their physical properties depending upon their source and refining process. Petrolatum obtained from different sources may therefore behave differently in a formulation. White petrolatum is a preferred petrolatum for use in cosmetics and pharmaceuticals, Additives, such as microcrystalline wax, may be used to add body to petrolatum.

The petrolatum used in the present invention was examined microscopically and no wax crystallization was observed. Thus, in one or more embodiments of the present invention the petrolatum selected shows no tendency to wax crystallization. In one or more further embodiments of the present invention the petrolatum based foamable carriers and compositions are free or substantially free of wax crystallization. In one or more further embodiments of the present invention the petrolatum based foamable carriers and compositions are free or substantially free of wax crystallization when the petrolatum level is about 50% to about 95% by weight in the composition before the addition of propellant.

MMP Inc state in their sales booklet on Sofinetic™ LMP (Rev 02/05 KVB) that they conducted studies with varying grades of petroleum USP to avoid formation of wax crystals in emulsions containing 20% petrolatum and that MMP's supersoft grade incorporated into low emulsifier content formulations containing 20% petroleum has been shown to eliminate undesirable crystallization of wax. They further state that when compared to similar compositions made with a higher melting point grade of petrolatum the Sofinetic™ LMP exhibited no tendency to wax crystalisation.

In certain embodiments, in the context of the present invention, the term petrolatum relates to any fatty substance, having rheological properties and meting temperature patterns in the same range as described above for petrolatum.

Since hyperhidrosis is often associated with an underlying disorder, a combination of an agent, suitable for the treatment of hyperhidrosis and an additional active agent, suitable for the treatment of the underlying disorder or another disorder which substantially concurrently occurs in the same patient is useful for simultaneous therapy of the patient's condition.

The foam product of the present invention is a pressurized preparation composed of formulation and propellant packed in aluminum canisters mounted with valve and actuator. Upon actuation of the foam onto the skin, the propellant immediately vaporizes and the emulsion deposits on the skin surface.

Examples of suitable propellants include volatile hydrocarbons such as butane, propane, isobutane and fluorocarbon gases, or mixtures thereof. In one embodiment butane, propane and isobutene is in the approximate ratio of 11:6:3 respectively.

In certain embodiments, fluorohydrocarbon propellants, other than chloro-fluoro carbons (CMCs) which are non-ozone-depleting propellants, are particularly useful in the production of a non-flammable foamable composition.

Such propellants include, but are not limited to hydrofluorocarbon (HFC) propellants, that contain no chlorine atoms, and as such, falls completely outside concerns about stratospheric ozone destruction by chlorofluorocarbons or other chlorinated hydrocarbons. Exemplary non-flammable propellants according to this aspect of the invention include propellants made by DuPont under the registered trademark Dymel, such as 1,1,1,2 tetrafluorethane (Dymel 134), and 1,1,1,2,3,3,3 heptafluoropropane (Dymel 227), 1,1, difluoro ethane (Dymel 152) and 1,1,1,3,3,3 hexafluoropropane. HFCs possess Ozone Depletion Potential of 0.00 and thus, they are allowed for use as propellant in aerosol products.

The propellant makes up about 3-25 wt % of the foamable composition. Aerosol propellants are used to generate and administer the foamable composition as a foam. The total composition including propellant, foamable compositions and optional ingredients is referred to as the foamable composition.

In one or more embodiments, the additional therapeutic agent is selected from the group consisting of an anti-infective, an antibiotic, an antibacterial agent, an antifungal agent, an antiviral agent, an antiparasitic agent, a steroidal antiinflammatory agent, a nonsterolidal anti-inflammatory agent, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and any mixture thereof.

The term modulating agent is used to describe an agent which can improve the stability of or stabilize a foamable carrier or composition and or an active agent by modulating the effect of a substance or residue present in the carrier or composition.

In one or more embodiments the modulating agent is used in a water in oil or oil in water emulsion. In one or more other embodiments the modulating agent is used in a waterless emulsion.

In certain embodiments the substance or residue may for example be acidic or basic and alter in an aqueous or potentially alter pH in a waterless environment or it may be one or more metal ions which may act as a potential catalyst in an aqueous or non aqueous environment.

In certain other embodiments the substance or residue may for example be acidic or basic and potentially alter an artificial pH in a waterless or substantially non aqueous environment or it may be one or more metal ions which may act as a potential catalyst in a waterless or substantially non aqueous environment.

In one or more embodiments the modulating agent is used to describe an agent which can affect pH in an aqueous solution. The agent can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the solvent to enable it to "mop up" or "lock" metal ions.

In an embodiment modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of an emulsion carrier, composition, foamable carrier or foamable composition or resultant foam of the present invention.

In other embodiments modulating agent is used to describe an agent which can effect pH in an aqueous solution the term modulating agent more particularly means an acid or base or buffer system or combinations thereof, which is introduced into or is present in and acts to modulate the ionic or polar characteristics and any acidity or basesity balance of a waterless or substantially non aqueous carrier, composition, foamable carrier or foamable composition or resultant foam of the present invention.

The substance or residue can be introduced into the formulation from any one or more of the ingredients, some of which themselves may have acidic or basic properties. For example the polymer or solvent may contain basic residues in which case it may be desirable or beneficial to add an acid. Alternatively the surfactant may contain some acid residues in which case the addition of a base may be desirable and beneficial. In some cases more than one ingredient may contain residues which may ameliorate or compound their significance. For example if one ingredient provided weak acid residues and another stronger acid residues the pH in an emulsion environment should be lower. In contrast if one residue was acid and the other basic the net effect in the formulation maybe significantly reduced. In some circumstances the active ingredient may favor an acidic pH or more significantly may need to be maintained at a certain acidic pH otherwise it may readily isomerize, chemically react or breakdown, in which case introducing acidic components such as an acidic polymer might be of help. In an embodiment of the present invention sufficient modulating agent is added to achieve a pH in which the active agent is preferably stable. In another embodiment of the present invention sufficient modulating agent is added to achieve an artificial pH in which the active agent is preferably stable.

The terms pH, pKa, and pKb, buffers and the like are used in classical measurements of an aqueous solution. Such measurements are artificial in a waterless environment. Nevertheless, reference to and description below of such terms are made for convenience and clarity, since such terms are well defined and understood with reference to aqueous solutions and further due to the lack of an appropriate uniform way of describing and identifying the artificial or virtual pH, pK etc in a waterless environment in relation to the present invention. Although predictions of artificial pH can be made using dilution techniques of measurements of waterless formulations diluted in water they are formulation sensitive and specific and have to be carefully calibrated with complex formulas.

Waterless medium can be polar and protic yet it does not conform to classical ionic behavior.

A buffer, as defined by Van Slyke [Van Slyke, *J. Biol. Chem.* 52, 525 (1922)], is "a substance which by its presence in solution increases the amount of acid or alkali that must be added to cause unit change in pH."

A buffer solution is a solution of a definite pH made up in such a way that this pH alters only gradually with the addition of alkali or acid. Such a solution consists of a solution of a salt of the week acid in the presence of the three acid itself. The pH of the solution is determined by the dissociation equilibrium of the free acid.

An acid can be a strong acid or a weak acid. A strong acid is an acid, which is a virtually 100% ionized in solution. In contrast, a week acid is one which does not ionize fully. When it is dissolved in water. The lower the value for pKa, the stronger is the acid and likewise, the higher the value for pKa the weaker is the acid.

A base can be a strong base or a weak base. A strong base is something, which is fully ionic with 100% hydroxide ions. In contrast, a weak base is one which does not convert fully into hydroxide ions in solution. The lower the value for pKb, the stronger is the base and likewise, the higher the value for pKb the weaker is the base.

In one or more embodiments of the present invention the modulating agent comprises an organic compound.

In one or more preferred embodiments of the present invention the chelating agent is selected from the group consisting of ethylenediaminetetraacetic acid (EDTA), diethylenetriaminepentaacetic acid (DTPA), hydroxyethylenediaminetriacetic acid (HEDTA), nitrilotriacetic acid (NTA), O,O'-bis(2-aminoethyl)ethyleneglycol-N,N,N',N'-tetraacetic acid (EGTA), trans-1,2-diaminocyclohexane-N,N,N',N'-tetraacetic acid (CyDTA) or a pharmaceutically acceptable salt thereof (normally as a sodium salt), more preferably EDTA, HEDTA and their salts; most preferably EDTA and its salts.

In one or more embodiments of the present invention a preferred non limiting example of the chelating agent is EDTA. Typically, the chelating and sequestering agent is present in the composition at a level of up to about 5.0%, preferably 1.0 percent, by weight, of the composition.

In one or more embodiments of the present invention the modulating agent may also be a preservative or an antioxidant or an ionization agent. Any preservative, antioxidant or ionization agents suitable for pharmaceutical or cosmetic application may be used. Non limiting examples of antioxidants are tocopherol succinate, propyl galate, butylated hydroxy toluene and butyl hydroxy anisol. Ionization agents may be positive or may be negative depending on the environment and the active agent or composition that is to be protected. Ionization agents may for example act to protect or reduce sensitivity of active agents. Non limiting examples of positive ionization agents are benzyl conium chloride, and cetyl pyridium chloride. Non limiting examples of negative ionization agents are sodium lauryl sulphate, sodium lauryl lactylate and phospholipids.

A humectant, is a substance that helps retain moisture and also prevents rapid evaporation. Non limiting examples are propylene glycol, propylene glycol derivatives, glycerin, hydrogenated starch hydrosylate, hydrogenated lanolin, lanolin wax, D manitol, sorbitol, sodium 2-pyrrolidone-5-carboxylate, sodium lactate, sodium PCA, soluble collagen, dibutyl phthalate, and gelatin. Non limiting preferred examples of suitable humectants are propylene glycol, propylene glycol derivatives, and glycerin. Further examples are provided elsewhere in the description. Other examples of humectants and moisturizers may be found in the Handbook of Pharmaceutical Additives published by Gower. Suitable ones for use with and soluble in the waterless and substantially waterless compositions of the present invention may be selected as will be appreciated by a person skilled in the art.

A moisturizer, is a substance that helps retain moisture or add back moisture to the skin. Examples are allantoin, petrolatum, urea, lactic acid, sodium PCV, glycerin, shea butter, caprylic/capric/stearic triglyceride, candelilla wax, propylene glycol, lanolin, hydrogenated oils, squalene, sodium hyaluronate and lysine PCA. Other examples may be found in the *Handbook of Pharmaceutical Additives* published by Gower.

Pharmaceutical compositions of the present invention may in one or more embodiments usefully comprise in addition a humectant or a moisturizer or combinations thereof.

The therapeutic foam of the present invention may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, preservatives, colorant and odorant agents and other formulation components, used in the art of formulation.

Additional component selected from the group consisting of an anti perspirant, an anti-static agent, a buffering agent, a bulking agent, a chelating agent, a colorant, a conditioner, a deodorant, a diluent, a dye, an emollient, fragrance, a humectant, an occlusive agent, a penetration enhancer, a perfuming agent, a permeation enhancer, a pH-adjusting agent, a preservative, a skin penetration enhancer, a sunscreen, a sun blocking agent, a sunless tanning agent, and a vitamins.

Aerosol propellants are used to generate and administer the foamable composition as a foam. The total composition including propellant, foamable compositions and optional ingredients is referred to as the foamable carrier. The propellant makes up about 3% to about 25 wt % of the foamable carrier. Examples of suitable propellants include volatile hydrocarbons such as butane, propane, isobutane or mixtures thereof, and fluorocarbon gases.

All % values are provided on a weight (w/w) basis.

Composition and Foam Physical Characteristics

A pharmaceutical or cosmetic composition manufactured using the foam carrier according to one or more embodiments of the present invention is very easy to use. When applied onto the afflicted body surface of mammals, i.e., humans or animals, it is in a foam state, allowing free application without spillage. Upon further application of a mechanical force, e.g., by gently rubbing the composition onto the body surface, it freely spreads on the surface and is rapidly absorbed.

The foam composition of the present invention creates a stable emulsion having an acceptable shelf-life of at least one year, or at least two years at ambient temperature. A feature of a product for cosmetic or medical use is long term stability. Propellants, which are a mixture of low molecular weight hydrocarbons, tend to impair the stability of emulsions. It has been observed, however, that emulsion foam compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing semi-solid hydrophobic solvents, e.g., white petrolatum, as the main ingredients of the oil phase of the emulsion, exhibit high viscosity and poor flowability and are inappropriate candidates for a foamable composition.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administratable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally-induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of less than 0.1 g/mL or less than 0.05 g/mL.

Fields of Pharmaceutical Applications

Hyperhidrosis is excessive sweating. Sweating is a natural phenomenon necessary for the regulation of an individual's body-temperature. The secretion of sweat, is mediated by a portion of our vegetative nervous system (the Sympathetic Nervous System). In some people, this system is working at a very high activity level, far higher than needed to keep a constant temperature. This condition is referred to as hyperhidrosis.

The composition of the present invention is suitable for the treatment of primary hyperhidrosis; i.e., hyperhidrosis with an unknown cause (idiopathic). The composition is also useful in secondary hyperhidrosis, wherein the hyperhidrosis is part of an underlying condition. Exemplary conditions that can involve and/or promote excessive sweating, typically involving the whole body, include hyperthyroidism or similar endocrine disorders; endocrine treatment for prostatic cancer or other types of malignant disorder; severe psychiatric disorders; obesity and menopause.

Thus, the foamable composition of the present invention is suitable for treating facial hyperhidrosis (sweat pouring down from the forehead); palmar hyperhidrosis (excessive sweating of the hands); axillary hyperhidrosis (hyperhidrosis of the armpits); plantar hyperhidrosis; hyperhidrosis of the trunk and/or the thighs; and facial hyperhidrosis; and any combination of them.

According to a survey conducted by the International Hyperhidrosis Society (IHHS) other "sweat inducing" circumstances include: eating spicy foods (32%), public speaking (28%), getting test results from a doctor (13%), taking an important test (8%), flying in an airplane (7%), telling a lie (6%) and returning a purchase to a store (3%).

In one or more embodiments, the foamable composition of the present invention is suitable for preventing or reducing the extent of excessive sweating.

In one or more embodiments, the foamable composition of the present invention is suitable an antiperspirant. In the context of the present invention, an antiperspirant effect is analogous to an effect against hyperhidrosis.

In certain embodiments, the foamable composition of the present invention is suitable for alleviating the smell, associated with excessive sweating.

Since secondary hyperhidrosis is invariably associated with an underlying disorder, a combination of an agent, suitable for the treatment of hyperhidrosis and an additional active agent, suitable for the treatment of the underlying disorder or another disorder which substantially concurrently occurs in the same patient is useful for simultaneous therapy of the patient's condition. By combining an appropriate antihyperhidrosis agent and optional active agents in the composition of the present invention, the composition is useful in treating a patient having any one of a variety of dermatological disorders, which include hyperydrosis as one or their symptoms, such as dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, eethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

Creaming

Formulation of emulsion foam is a very delicate balance between the functional inactive ingredients, excipients, which contribute to droplet size, separating film, viscosity and stability. In order to assure accurate and continuous foam actuation, the Foam Formulation should preferably be liquid and shakable in the canister, otherwise it will not flow easily and completely towards and through the valve. In the context of certain foamable formulations like petrolatum it is possible as an exception for the composition to be marginally or apparently non shakable whilst the composition has a sufficient degree of flowability under pressure of the propellant that it is possible to obtain a good quality of foam.

Stability of emulsions and resilience to creaming is desired. In the context of foamable emulsion compositions, for example in which petrolatum is a significant component it has been discovered that improved physical stability is obtained by an appropriate choice of product viscosity through use of different blends of polyethylene glycols or propylene glycol plus a surfactant or surfactant system optionally in combination with stabilizing agents and or viscoelastic agents, which can provide suitable rheology whilst retaining the requirements of shakability or at least flowability and by controlling droplet size.

By creaming it is meant that particles of the disperse phase concentrate in the upper layer, form a cream-like concentrated emulsion. The creaming value is defined as the relative volume of the creamed phase and the total volume the sample. The expression used for calculation of the creaming volume is as follows:

$$\% \text{ Creaming} = \frac{V_{Creamed\ Phase}}{V_{total}} \times 100$$

Creaming values are between 1% and 99%, accordingly. 100% means "no creaming" which is the desirable best score. 0% (Zero value) indicates phase separation and is the worst score.

By physically durable in the context of the hyperhidrosis compositions it is intended that the formulation is capable of physically withstanding partially, or to some or to a substantial degree at least one of centrifugation at 3000 rpm for at least 10 minutes such that no emulsion phase separation occurs;

In a preferred embodiment the emulsion composition should exhibit pseudoplastic rheological behavior.

By selective use of appropriate stabilizing surfactant, co-surfactants and optionally stabilizing polymers the emulsion compositions of the present invention can be stabilized.

By appropriate selection of agents, surfactants and solvent in an emulsion composition to facilitate biocompatibility and to achieve the appropriate balance of physical properties, it is possible to prepare formulations that are resilient to creaming or to phase separation either partially or to some or to a substantial degree when subjected to centrifugation.

Methodology

A general procedure for preparing foamable compositions is set out in WO 2004/037225, which is incorporated herein by reference.

Emulsion Foam, Method (a)
1. Mix oily phase ingredients and heat to 75° C. to melt all ingredients and obtain homogeneous mixture.
2. Mix polymers in water with heating or cooling as appropriate for specific polymer.
3. Add all other water soluble ingredients to water-polymer solution and heat to 75° C.
4. Add slowly internal phase to external phase at 75° C. under vigorous mixing and homogenize to obtain fine emulsion.
5. Cool to below 40° C. and add sensitive ingredients with mild mixing.
6. Cool to room temperature.

Emulsion Foam, Method (b)
1. Mix oily phase ingredients and heat to 75° C. to melt all ingredients and obtain homogeneous mixture.
2. Mix polymers in water with heating or cooling as appropriate for specific polymer.
3. Add all other water soluble ingredients to water-polymer solution and heat to 75° C.
4. Add slowly external phase to internal phase at 75° C. under vigorous mixing and homogenize to obtain fine emulsion.
5. Cool to below 40° C. and add sensitive ingredients with mild mixing.
6. Cool to room temperature.

Waterless Foam
1. Dissolve the polymers in the main solvent with heating or cooling as appropriate for specific polymer. Add the all other ingredients and heat to 75° C. to melt and dissolve the various ingredients.
2. Cool to below 40° C. and add sensitive ingredients with mild mixing.

3. Cool to room temperature.

Oily Waterless Foam
1. Mix all ingredients excluding polymers and heat to 75° C. to melt and dissolve and obtain homogeneous mixture.
2. Mix well and cool to below 40° C. and add the polymers and sensitive ingredients with moderate mixing.
3. Cool to room temperature.

Oily Foam with Phospholipids and/or Water
1. Swell the phospholipids in the main oily solvent under mixing for at least 20 minutes until uniform suspension is obtained.
2. Add all other ingredients excluding polymers and heat to 75° C. to melt and dissolve and obtain homogeneous mixture.
3. Mix well and cool to below 40° C. and add the polymers and sensitive ingredients with moderate mixing.
4. Cool to room temperature.
5. In case of polymers dissolved in water or organic solvent, dissolve the polymers in the solvent with heating or cooling as appropriate for specific polymer and add to the oily mixture under vigorous mixing at ~40° C.

Petrolatum (Water/Oil) Emulsion
Step 1: Preparation of Water Phase
The water is heated to 70° C.
Step 2: Preparation of Oil Phase
The Oil Phase is prepared by mixing together of all ingredients and heat up to 70° C. Continue mixing until full melting for solid ingredients.
Step 3: PFF Formation
Step 3-a: Emulsification
The Water phase at 70-75° C. is added to the Oil phase in small portions at 70° C. The emulsification is performed in presence of vigorous agitation continues until PFF uniformity is reached for at least 20 min.
Step 4: Addition of Active Agent
Stop heating the PFF and slow addition of active agent at 40-50° C. during vigorous mixing. Continue mixing for at lease 30 min.
Step 5: Canisters Filling and Crimping
Each aerosol canister is filled with PFF and crimped with valve using vacuum crimping machine.
Step 6: Pressurizing
Step 6-a: Propellant Filling
Pressurizing is carried out using a gas mixture.
Canisters are filled and then warmed for 30 sec in a warm bath at 50° C. and well shaken immediately thereafter
Step 6-b: Closure Integrity Test.
Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.
For sensitive ingredients cool to below 40° C. and add them with mild mixing.

Petrolatum (Solvent/Oil) Emulsion
The procedure is as above for water in petrolatum emulsion, but, DMI, or PG, or PEG 400 replaces the water.

Petrolatum (Waterless)
Step 1: Preparation of Oil Phase
The Oil Phase is prepared by mixing together of all ingredients and heat up to 65° C. Continue mixing until full melting for solid ingredients.
Step 2: Addition of active agent
Stop heating the oil phase and slow addition of active agent at 40-50° C. during vigorous mixing. Continue mixing for at lease 30 min.

Step 5: Canisters Filling and Crimping
Each aerosol canister is filled with PFF and crimped with valve using vacuum crimping machine.
Step 6: Pressurizing
Step 6-a: Propellant Filling
Pressurizing is carried out using a gas mixture.
Canisters are filled and then warmed for 30 sec in a warm bath at 50° C. and well shaken immediately thereafter
Step 6-b: Closure Integrity Test.
Each pressurized canister is subjected to bubble and crimping integrity testing by immersing the canister in a 60° C. water bath for 2 minutes. Canisters are observed for leakage as determined by the generation of bubbles. Canisters releasing bubbles are rejected.
For sensitive ingredients cool to below 40° C. and add them with mild mixing.

Tests
By way of non limiting example the objectives of hardness, collapse time and FTC stability tests are briefly set out below as would be appreciated by a person of the art.

Hardness
LFRA100 instrument is used to characterize hardness. A probe is inserted into the test material. The resistance of the material to compression is measured by a calibrated load cell and reported in units of grams on the texture analyzer instrument display. Preferably at least three repeat tests are made. The textural characteristics of a dispensed foam can effect the degree of dermal penetration, efficacy, spreadability and acceptability to the user. The results can also be looked at as an indicator of softness. Note: the foam sample is dispensed into an aluminum sample holder and filled to the top of the holder.

Collapse Time
Collapse time (CT) is examined by dispensing a given quantity of foam and photographing sequentially its appearance with time during incubation at 36° C. It is useful for evaluating foam products, which maintain structural stability at skin temperature for at least 1 min.

FTC
To check the foam appearance under extreme conditions of repeated cycles of cooling, heating, (first cycle) cooling, heating (second cycle) etc., commencing with −100° C. (24 hours) followed by +400° C. (24 hours) measuring the appearance and again repeating the cycle for up to three times.

Creaming by Centrifugation:
1. Principle of Test
The centrifugation used in this procedure serves as a stress condition simulating the aging of the liquid dispersion under investigation. Under these conditions, the centrifugal force applied facilitates the coalescence of dispersed globules or sedimentation of dispersed solids, resulting in loss of the desired properties of the formulated dispersion.
2. Procedure
2.1. Following preparation of the experimental formulation/s, allow to stand at room temperature for $\geq 24$ h.
2.2. Handle pentane in the chemical hood. Add to each experimental formulation in a 20-mL glass vial a quantity of pentane equivalent to the specified quantity of propellant for that formulation, mix and allow formulation to stand for at least 1 h and not more than 24 h.
2.3. Transfer each mixture to 1.5 mL microtubes. Tap each microtube on the table surface to remove entrapped air bubbles.

2.4. Place visually balanced microtubes in the centrifuge rotor and operate the centrifuge at 3,000 rpm for 10 min or at 10,000 rpm for 10 min.

EXAMPLES

Oil in Water Platform

Example 1

Oil in Water Foamable Compositions (~12% Oil) Including Dicarboxylic Acids and Derivatives Thereof

| Ingredient | Composition No: | | | |
|---|---|---|---|---|
| | AZ-1 | DA-2 | DA-3 | DA-4 |
| | % | | | |
| Azelaic acid | 15.00 | | | |
| Dimethyl azelate | | 10.00 | | |
| Di(ethyl salicylate) azelate (TU-2100) | | | 10.00 | |
| Sebacic acid | | | | 10.00 |
| Mineral oil | 5.60 | 5.60 | 5.60 | 5.60 |
| Isopropyl palmitate | 5.60 | 5.60 | 5.60 | 5.60 |
| Sorbitan stearate (Span 60) | 2.00 | 2.00 | 2.00 | 2.00 |
| PPG15-stearyl ether | 1.00 | 1.00 | 1.00 | 1.00 |
| Stearic acid | 0.85 | 0.85 | 0.85 | 0.85 |
| Glyceryl monostearate | 0.45 | 0.45 | 0.45 | 0.45 |
| Xanthan gum | 0.26 | 0.26 | 0.26 | 0.26 |
| Methocel K100M | 0.26 | 0.26 | 0 | 0 |
| Preservative | 0.25 | 0.25 | 0.25 | 0.25 |
| Propellant | 10.00 | 10.00 | 10.00 | 10.00 |
| Water | To 100 | To 100 | To 100 | To 100 |

Example 2

Oil in Water Foamable Compositions (~12% Oil)

| Ingredient | % w/w |
|---|---|
| Caprylic/Capric Triglyceride | 10.87 |
| Cetostearyl alcohol | 1.09 |
| Glyceryl stearate | 0.54 |
| Benzoic acid | 0.10 |
| PEG-40 Stearate | 2.83 |
| Methylcellulose A4M | 0.11 |
| Xanthan gum | 0.27 |
| Polysorbate 80 | 0.98 |
| Water, purified | 51.90 |
| Dimethyl isosorbide | 5.44 |
| Propylene Glycol | 10.87 |
| Azelaic acid | 15.00 |
| | 100.00 |
| NaOH (18% solution) | to pH = 4.5 |
| Propellant | 8 |
| RESULTS | |
| Quality | Good |
| Viscosity, at 10 rpm (cP) | 5,961 |
| Centrifugation, 3,000 rpm for 10 min | No phase separation |
| Centrifugation, 10,000 rpm for 10 min | No phase separation |
| Density | 0.036 |

Example 3

Oil in Water Foamable Compositions with an Active Agent

| Ingredients | 6B | 3B |
|---|---|---|
| Aluminum zirconium trichlorohydrex-glycine | 10.00 | 10.00 |
| Mineral oil light | | 5.04 |
| Isopropyl myristate | | 5.04 |
| Glyceryl monostearate | | 0.41 |
| Propylene glycol | 9.78 | 0.41 |
| Stearyl alcohol | | 0.77 |
| Dimethyl isosorbide | 4.90 | |
| Purified water | 60.21 | 74.73 |
| Methylcellulose A4M | 0.10 | |
| Methylcellulose K100 | | 0.23 |
| Xanthan gum | 0.24 | 0.23 |
| Polysorbate 80 | 0.88 | 0.81 |
| Caprylic/Capric Triglyceride | 9.78 | |
| Cetearyl alcohol | 0.98 | |
| Glyceryl stearate | 0.49 | |
| Benzoic acid | 0.09 | |
| PEG-40 Stearate | 2.55 | 2.34 |
| Total | 100.00 | 100.00 |
| Propellant | 8.00 | 8.00 |
| RESULTS | | |
| Foam quality | Excellent | Excellent |

Example 4

Oil in Water Foamable Compositions with Two Active Agents

| Ingredients | 3B |
|---|---|
| Aluminum zirconium trichlorohydrex-glycine | 10.00 |
| Naproxen | 1.00 |
| Mineral oil light | 4.98 |
| Isopropyl myristate | 4.98 |
| Glyceryl monostearate | 0.40 |
| Propylene glycol | 0.40 |
| Stearyl alcohol | 0.76 |
| Purified water | 73.90 |
| Methylcellulose K100 | 0.23 |
| Xanthan gum | 0.23 |
| Polysorbate 80 | 0.80 |
| PEG-40 Stearate | 2.31 |
| Total | 100.00 |
| Propellant | 8.00 |
| RESULTS | |
| Foam quality | Excellent |

Note the composition may be reformulated with only one active agent

Example 5

Theoretical Oil in Water Foamable Compositions with Two Active Agents

| Ingredients | |
|---|---|
| Aluminum zirconium trichlorohydrex-glycine | 10.00 |
| Glycopyrrolate | 1.00 |
| Mineral oil light | 4.98 |
| Isopropyl myristate | 4.98 |
| Glyceryl monostearate | 0.40 |
| Propylene glycol | 0.40 |
| Stearyl alcohol | 0.76 |
| Purified water | 73.90 |
| Methylcellulose K100 | 0.23 |
| Xanthan gum | 0.23 |
| Polysorbate 80 | 0.80 |
| PEG-40 Stearate | 2.31 |
| Total | 100.00 |
| Propellant | 8.00 |

Note the composition may be reformulated with only one active agent. Glycopyrrolate may be applied at up to about 6%, preferably up to about 4% although at higher levels side effects may be observed. As will be appreciated the water and or aluminum salt may be for example reduced by the amount the glycopyrrolate is increased.

Example 6

Oil in Water Foamable Compositions (~30% Oil) Including Dicarboxylic Acids and Derivatives Thereof

| Ingredient | AZ-2 | DA-5 | DA-6 | DA-7 |
|---|---|---|---|---|
| | % | | | |
| Azelaic acid | 15.00 | | | |
| Dimethyl azelate | | 5.00 | | |
| Di(ethyl salicylate) azelate (TU-2100) | | | 10.00 | |
| Sebacic acid | | | | 10.00 |
| MCT oil | 30.00 | 30.00 | 30.00 | 30.00 |
| Glyceryl monostearate | 0.50 | 0.50 | 0.50 | 0.50 |
| Stearyl alcohol | 1.00 | 1.00 | 1.00 | 1.00 |
| Xanthan gum | 0.30 | 0.30 | 0.30 | 0.30 |
| Methocel K100M | 0.30 | 0.30 | 0.30 | 0.30 |
| Polysorbate 80 | 1.00 | 1.00 | 1.00 | 1.00 |
| PEG-40 stearate | 3.00 | 3.00 | 3.00 | 3.00 |
| Cocamidopropyl betaine | 0.50 | 0.50 | 0.50 | 0.50 |
| Preservative | 0.25 | 0.25 | 0.25 | 0.25 |
| Propellant | 16.00 | 16.00 | 16.00 | 16.00 |
| Water | To 100 | To 100 | To 100 | To 100 |

Example 7

A Matrix of Compositions Comprising Hydrocortisone and Azelaic Acid (AZL) as Active Agents, which are Resilient to Creaming

| Chemical name | W/W % | W/W % | W/W % | W/W % |
|---|---|---|---|---|
| Caprylic/Capric Triglyceride | 5.00 | 10.00 | 10.00 | 10.00 |
| Cetearyl alcohol | 0.90 | 1.00 | 1.00 | 1.00 |
| Glyceryl stearate | 0.45 | 0.50 | 0.50 | 0.50 |
| Cholesterol | 1.00 | 1.00 | | |
| Benzyl alcohol | 1.00 | | | 1.00 |
| Benzoic acid | | 0.20 | 0.20 | |
| Butylated hydroxytoluene | 0.10 | 0.10 | 0.10 | 0.10 |
| PEG-40 Stearate | 2.60 | 2.60 | 2.60 | 2.60 |
| Methylcellulose K100M | 0.10 | | 0.10 | 0.10 |
| Methylcellulose A4M | | 0.10 | | |
| Xanthan gum | 0.25 | 0.25 | 0.25 | 0.25 |
| Polysorbate 80 | 0.90 | 0.90 | 0.90 | 0.90 |
| EDTA disodium | 0.10 | | | |
| Sodium Hydroxide | | | | 0.50 |
| Water purified | 55.60 | 57.35 | 53.35 | 67.05 |
| Dimethyl isosorbode | 10.00 | | 5.00 | |
| Propylene glycol | 6.00 | 5.00 | 10.00 | |
| PEG-400 | | 5.00 | | |
| Azelaic Acid | 15.00 | 15.00 | 15.00 | 15.00 |
| Hydrocortisone | 1.00 | 1.00 | 1.00 | 1.00 |
| Total | 100 | 100 | 100 | 100 |
| Results Appearance: | | | | |
| Quality | E | E | E | E |
| Color | O.W | O.W | O.W | O.W |
| Odor | V.F.O | V.F.O | V.F.O | V.F.O |
| Collapse time | >120 | >120 | >120 | >120 |
| Hardness | 22.3 | 21.3 | 39.0 | 14.5 |
| Density | 0.038 | 0.030 | 0.032 | 0.044 |
| Centrifugation 3K 10 min | Stable* | Stable* | Stable* | Stable* |
| Centrifugation 10K 10 min | 10% Creaming | 40% Creaming | 30% Creaming | 20% Creaming |

*Stable = no phase separation or creaming were observed;
E = excellent;
OW = off white; and
V.F.O = very faint odor.

Comments: It is very difficult to stabilize such compositions since azelic acid is a solid and significant quantities are required. Hydrocortisone in combination with azaleic acid were successfully formulated in oil-in-water emulsions. The formulations produced foams of excellent quality with beneficial physical properties such as desired hardness, a reasonable collapse time of over two minutes during which the expanded foam remains substantially intact, and resistance to creaming/phase separation when subjected to centrifugation at 3000 rpm. It can be extrapolated that compositions, which can withstand such a g-force are probably capable of remaining physically stable at room temperature during the expected two years shelf life of a pharmaceutical product or for a lesser reasonable period. These compositions were rugged and resilient to harsh centrifugation of 10,000 rpm.

Example 8

A Matrix of Compositions Comprising Fluocinonide and Azelaic Acid (AZL) as Active Agents, which are Resilient to Creaming

| Chemical name | W/W % | W/W % | W/W % | W/W % |
|---|---|---|---|---|
| Caprylic/Capric Triglyceride | 5.00 | 10.00 | 10.00 | 10.00 |
| Cetearyl alcohol | 0.90 | 1.00 | 1.00 | 1.00 |
| Gleceryl stearate | 0.45 | 0.50 | 0.50 | 0.50 |
| Cholesterol | 1.00 | 1.00 | | |
| Benzyl alcohol | 1.00 | | | 1.00 |
| Benzoic acid | | 0.20 | 0.20 | |
| Butylated hydroxytoluene | 0.10 | 0.10 | 0.10 | 0.10 |
| PEG-40 Stearate | 2.60 | 2.60 | 2.60 | 2.60 |
| Methylcellulose K100M | 0.10 | | 0.10 | 0.10 |
| Methylcellulose A4M | | 0.10 | | |
| Xanthan gum | 0.25 | 0.25 | 0.25 | 0.25 |
| Polysorbate 80 | 0.90 | 0.90 | 0.90 | 0.90 |
| EDTA disodium | 0.10 | | | |
| Sodium Hydroxide | | | | 0.50 |
| Water purified | 56.50 | 58.25 | 54.25 | 67.95 |
| Dimethyl isosorbode | 10.00 | | 5.00 | |
| Propylene glycol | 6.00 | 5.00 | 10.00 | |
| PEG-400 | | 5.00 | | |
| Azelaic Acid | 15.00 | 15.00 | 15.00 | 15.00 |
| Fluocinonide | 0.10 | 0.10 | 0.10 | 0.10 |
| Total | 100 | 100 | 100 | 100 |
| Results | A | B | C | D |
| Appearance: | | | | |
| Quality | E | E | E | E |
| Color | Off white | Off white | Off white | Off white |
| Odor | V.F.O* | V.F.O* | V.F.O* | V.F.O* |
| Collapse time | >120 | >120 | >120 | >120 |
| Hardness | 22.3 | 21.3 | 39.0 | 14.5 |
| Density | 0.038 | 0.030 | 0.032 | 0.044 |
| Centrifugation 3K 10 min | Stable** | Stable** | Stable** | Stable** |
| Centrifugation 10K 10 min | 10% Creaming | 40% Creaming | 30% Creaming | 20% Creaming |

*Stable = no phase separation or creaming;
E = excellent;
V.F.O = very faint odor.

Comments: fluocinonide in combination with azelaic acid were formulated in oil-in-water emulsions based on caprylic/capric triglyceride. The 15% azelaic acid suspension with fluocinonide shows minimal settling and azelaic acid particles in the emollient emulsion are readily re-suspendable upon slight hand shaking. The formulations produced foams of excellent quality with beneficial physical properties such as desired hardness, a reasonable collapse time of over two minutes during which the expanded foam remains substantially intact, and resistance to creaming/phase separation when subjected to centrifugation at 3000 rpm. It can be extrapolated that compositions, which can withstand such a g-force are probably capable of remaining physically stable at room temperature during the expected two years shelf life of a pharmaceutical product or for a lesser reasonable period.

Example 9

Theoretical Oil in Water Foamable Compositions Including Agents Suitable for the Treatment of Hyperhidrosis

| | Composition No: | | | |
|---|---|---|---|---|
| | AZ-1 | AC-2 | ZC-3 | BT-4 |
| Ingredient | % | | | |
| Azelaic acid | 15.00 | | | |
| Aluminum chloride | | 10.00 | | |
| Zirconium chloride | | | 10.00 | |
| Botulism toxin | | | | 2.00 |
| Mineral oil | 5.60 | 5.60 | 5.60 | 5.60 |
| Isopropyl palmitate | 5.60 | 5.60 | 5.60 | 5.60 |
| Sorbitan stearate (Span 60) | 2.00 | 2.00 | 2.00 | 2.00 |
| PPG15-stearyl ether | 1.00 | 1.00 | 1.00 | 1.00 |
| Stearic acid | 0 | 0 | 0.85 | 0.85 |
| Stearyl alcohol | 0.85 | 0.85 | | |
| Glyceryl monostearate | 0.45 | 0.45 | 0.45 | 0.45 |
| Xanthan gum | 0.26 | 0.26 | 0.26 | 0.26 |
| Methocel K100M | 0.26 | 0.26 | 0 | 0 |
| Preservative | 0.25 | 0.25 | 0.25 | 0.25 |
| Water | To 100 | To 100 | To 100 | To 100 |
| Propellant | 10.00 | 10.00 | 10.00 | 10.00 |

Example 10

Water in Oil Nonsteroidal Immunomodulating Compositions

| | Composition Code: | | | | | |
|---|---|---|---|---|---|---|
| | WO-1 | WO-2 | WO-3 | WO-4 | WO-5 | WO-6 |
| Ingredient | % | | | | | |
| Etodolac (active agent) | 1.00 | | | | | |
| Tacrolimus (active agent) | | 2.00 | | | | |
| Ketoconazole (active agent) | | | 2.00 | | | |
| Salicylic acid (active agent) | | | | 5.00 | | |
| Azelaic acid (active agent) | | | | | 15.00 | |
| Thalidomide (active agent) | | | | | | 4.00 |
| Clindamycin (additional active agent) | | | | 2.00 | 2.00 | |
| Mineral oil | 12.00 | 12.00 | 12.00 | 12.00 | 12.00 | 10.00 |

-continued

| Ingredient | WO-1 | WO-2 | WO-3 | WO-4 | WO-5 | WO-6 |
|---|---|---|---|---|---|---|
| | | | % | | | |
| Isopropyl myristate | 12.00 | 12.00 | 12.00 | 12.00 | 12.00 | 10.00 |
| Dimeticone V100 | 3.00 | 3.00 | 3.00 | 3.00 | 3.00 | |
| Glyceryl monostearate | 0.50 | 0.50 | 0.50 | 0.50 | 0.50 | 0.50 |
| Zinc oxide | 10.00 | 15.00 | 15.00 | 20.00 | 25.00 | |
| Titanium Dioxide | | | | | | 20.00 |
| Alpha-Bisabolol | 0.20 | 0.20 | 0.20 | 0.20 | 0.20 | |
| MYRJ 52 | 3.00 | 3.00 | 3.00 | 3.00 | 3.00 | 3.00 |
| Microcrystalline cellulose + carboxymethyl cellulose) | 2.00 | 1.00 | 2.00 | 2.00 | 2.00 | 2.00 |
| TWEEN 80 | 1.00 | 1.00 | 1.00 | 1.00 | 1.00 | 1.00 |
| Cocoamidopropylbethaine | 0.50 | 0.50 | 0.50 | 0.50 | 0.50 | 0.50 |
| D-Panthenol 50P | 10.00 | 10.00 | 10.00 | 10.00 | 10.00 | |
| Preservative | 0.30 | 0.30 | 0.30 | 0.30 | 0.30 | 0.30 |
| Purified water | To 100 | To 100 | To 100 | To 100 | To 100 | To 100 |

Example 11

Emollient+25% Petrolatum+10% Aluminum Chlorohydrate

| Ingredient name (INCI, CTFA) | | Concentration % w/w |
|---|---|---|
| Water | Solvent | 59.00 |
| Petrolatum | Occlusive Agent | 25.00 |
| C14-22 Alcohol & C12-20 Alkyl Glucoside | Emulsifier | 3.00 |
| Aluminum starch octenylsuccinate (ASOS) | Polymer | 3.00 |
| Aluminium chlorohydrate | Anti perspiration agent | 10 |
| Total | | 100.00 |
| Propellant (Propane/Butane/Isobutane) | | 8.00 |

Example 12

The Effect of the Above Petrolatum Formulation on the Perspiration of a Subject was Measured with and without Aluminium Chlorohydrate Perspiration Study
Description The Foamix Foam formulations are provided in and dispensed from a pressurized aerosol can or as a pre-foam formulation (PFF).
Treatment Regimen 0.5 gm of the foam containing active ingredient is applied on the sole of one foot and 0.5 gm of placebo (as PFF) is applied on the sole of the other foot.
Method of Measuring Subject is to remove the shoes and socks from his feet and the formulation is spread on the sole of the feet. Subject is to sit with his feet up, such that there is no physical contact between the feet and the environment until complete absorption of the foam or placebo. A moisture absorbing material (M.A.M.) is weighed and placed on the sole of each foot. The M.A.M. is covered by nylon, an occlusive material. The nylon is attached to the feet by scotch tape. Socks and shoes are replaced and the subject is to continue his/her normal activities. After six hours the M.A.M. is recovered and weighed. The difference in weight of the MAM at zero time and after six hours is the result.

Prior and Concurrent Therapy

No prior or concurrent therapy is permitted from 24 hours prior to the initiation of the study until the study is completed.
Stock Compositions Non-limiting examples of how stock solutions are made up with and without API. Other stock solutions may be made using the same methodology by simply varying adding or omitting ingredients as would be appreciated by one of the ordinary skills in the art. Propellant is added. The propellant is a mixture of butane, propane, isobutane The results are:

| | Time point | | |
|---|---|---|---|
| Parameters | ZT | After 6 hours | Delta (after 6 hours value − ZT value) |
| Leg Treated with API | 4.53 g | 4.97 g | 0.44 g |
| Leg treated with corresponded placebo | 5.62 g | 6.17 g | 0.55 g |

Note, as the placebo contained ASOS, which is a source of aluminium it may itself have some anti hyperhidrosis effect. Thus, it may be that the 20% difference in perspiration observed between the active and placebo formulations in the same subject may be more pronounced in the absence of ASOS.

Example 13

Water in Petrolatum Composition with Two API's

| Ingredients | 9A | 9B |
|---|---|---|
| Aluminum zirconium trichlorohydrex-glycine | 10.00 | 10.00 |
| Piroxicam | 1.00 | |
| Naproxen | | 1.00 |
| Petrolatum (Sofmetic LMF) | 48.95 | 48.95 |
| Petrolatum white (Pioner 5464) | 17.80 | 17.80 |
| Glyceryl monostearate | 0.45 | 0.45 |

| Ingredients | 9A | 9B |
|---|---|---|
| Water, purified | 19.85 | 19.85 |
| Carboxymethyl cellulose | 0.18 | 0.18 |
| Polysorbate 20 | 0.89 | 0.89 |
| Glycerin | 0.89 | 0.89 |
| Total product: | 100.00 | 100.00 |
| Propellant | 20.00 | 20.00 |
| Results | | |
| Foam quality | Good | Good |

Example 14

Theoretical Water in Petrolatum Composition with Two API's

| Ingredients | |
|---|---|
| Aluminum zirconium trichlorohydrex-glycine | 10.00 |
| Glycopyrrolate | 1.00 |
| Petrolatum (Sofmetic LMF) | 48.95 |
| Petrolatum white (Pionier 5464) | 17.80 |
| Glyceryl monostearate | 0.45 |
| Water, purified | 19.85 |
| Carboxymethyl cellulose | 0.18 |
| Polysorbate 20 | 0.89 |
| Glycerin | 0.89 |
| Total product: | 100.00 |
| Propellant | 20.00 |

Note the composition may be reformulated with only one active agent. Glycopyrrolate may be applied at up to about 6%, preferably up to about 4% although at higher levels side effects may be observed. As will be appreciated the petrolatum and or aluminum salt may be for example reduced by the amount the glycopyrrolate is increased.
Petrolatum Waterless

Example 15

Petrolatum Based Waterless Foam with Different API's

| 15a. Stock Waterless | |
|---|---|
| Ingredients Ingredient | Stock Waterless w/w % |
| Petrolatum (Sofmetic ™ LMP) | 58.82 |
| Petrolatum white (Pionier 5464) | 31.76 |
| Glyceryl monostearate | 1.76 |
| Stearyl alcohol | 2.94 |
| Myristyl alcohol | 2.35 |
| Polysorbate 20 | 2.35 |
| Total product: | 100.00 |
| Propellant: n-butane | 20.00 |
| Results | |
| Shakability | yes |
| Foam quality | Good |
| Color | Transparent-white |

| 15a. Stock Waterless | |
|---|---|
| Ingredients Ingredient | Stock Waterless w/w % |
| Odor | No odor |
| Hardness (g) | 87.88 |
| Collapse Time (sec) | >300 |
| Viscosity (cP) | 118,174 |
| Centrifugation 3000 rpm | Stable |
| Washable | No |

Comments: This formula was prepared in a pressurized glass bottle and a translucent single phase was observed with the propellant being dissolved in the petrolatum. See FIG. 1.

The formula produced good quality foam.

| 15b. Stock Waterless + API's | | | |
|---|---|---|---|
| Ingredients Ingredient | 16 w/w % | 17 w/w % | 18 w/w % |
| Stock PFF | 99.88 | 95.00 | 85.00 |
| Betamethasone 17 valerate micronized | 0.12 | | |
| Acyclovir | | 5.00 | |
| Azelaic acid | | | 15.00 |
| Total product: | 100.00 | 100.00 | 100.00 |
| Propellant: n-butane | 20.00 | 20.00 | 20.00 |
| Results | | | |
| Shakability | yes | yes | yes |
| Foam quality | Good | Good+ | Good+ |

Example 16

Waterless Oleaginous+10% Aluminum Chlorohydrate

| Ingredient name | Function | Concentration % w/w |
|---|---|---|
| PPG-15 Stearyl Ether | Emulsifier | 13.05 |
| Octyldodecanol | Oil | 10.8 |
| Oleyl alcohol | Oil | 4.5 |
| Heavy Mineral Oil | Oil | 7.2 |
| Light mineral oil | Oil | 24.75 |
| Glyceryl monostearate, Stearyl alcohol, Cetyl Palmitate & Cocoglyceride | Emulsifier | 8.1 |
| Methyl glucose sesquiestearate | Emulsifier | 2.7 |
| Myristyl alcohol | | 1.35 |
| Polyoxyl 21 stearyl Ether | Emulsifier | 2.25 |
| Polyoxyl 2 stearyl Ether | Emulsifier | 4.5 |
| Hydrogenated Castor Oil | Oil | 1.8 |
| Diidsopropyl adipate | Oil | 4.5 |
| Aluminum starch Octenilsuccinate | Polymer | 4.5 |
| Alluminium chlorohydrate | Anti perspiration agent | 10 |
| Total | | 100 |
| (Propane/Butane/Isobutane) | | 8 |

Example 17

PEG 400+10% Aluminum Chlorohydrate

| Ingredient name | Function | Concentration % w/w |
|---|---|---|
| PEG-400 | Solvent | 86.00 |
| Hydroxypropyl cellulose | Polymer | 2.00 |
| Steareth-2 | Emulsifier | 2.00 |
| Alluminium chlorohydrate | Anti perspiration agent | 10 |
| Total | | 100 |
| Mixture of Propane, butane and Isobutane | | 8.00 |

Note

PEG 400 can be substituted by other PEG,s like PEG 200 or PEG 600 or mixtures thereof and small amounts of higher molecular weight PEG be added if is appropriate to make the composition more viscous. Propylene glycol can be used instead of PEG. Mixtures of PEG(s) and PG can also be used.

Example 18

PEG 400+10% Aluminum Zirconium Trichlorohydrex-Glycine

| Ingredients | 5B | 7B | 8B |
|---|---|---|---|
| Aluminum zirconium trichlorohydrex-glycine | 10.00 | 10.00 | 10.00 |
| Hydroxypropyl cellulose | 0.45 | 1.80 | 0.45 |
| Polyethylene glycol 400 | 87.75 | 86.40 | 88.65 |
| Steareth 2 | 1.80 | 1.80 | 0.90 |
| Total | 100.00 | 100.00 | 100.00 |
| Propellant | 8.00 | 8.00 | 8.00 |
| RESULTS | | | |
| Foam quality | Good | Good | Good |

PEG 400 can be substituted by other PEG,s like PEG 200 or PEG 600 or mixtures thereof and small amounts of higher molecular weight PEG be added if is appropriate to make the composition more viscous. Propylene glycol can be used instead of PEG. Mixtures of PEG(s) and PG can also be used. Waterless Propylene Glycol

Example 19

PG+10% Aluminum Zirconium Trichlorohydrex-Glycine

| Ingredients | 2B | 4B |
|---|---|---|
| Aluminum zirconium trichlorohydrex-glycine | 10.00 | 10.00 |
| Propylene glycol | 41.40 | 81.90 |
| Glycerin anhydrous | 29.70 | 0.00 |
| Stearyl alcohol | 0.90 | 1.80 |
| Hydroxypropyl cellulose | 1.35 | 1.80 |
| Laureth-4 | 1.80 | 1.80 |
| Glyceryl Monostearate/PEG 100 Stearate | 1.35 | 2.70 |
| Dimethyl isosorbide | 13.50 | |
| Total | 100.00 | 100.00 |
| Propellant | 8.00 | 8.00 |
| RESULTS | | |
| Foam quality | Good | Good |

Note the composition can be reformulated with PEG or mixture of PEGs instead of PG. Mixtures of PEG(s) and PG can also be used.

Example 20

Propylene Glycol Based Composition with Two Active Agents

| Ingredients | 4B |
|---|---|
| Aluminum zirconium trichlorohydrex-glycine | 10.00 |
| Piroxicam | 1.00 |
| Propylene glycol | 81.79 |
| Stearyl alcohol | 1.60 |
| Hydroxypropyl cellulose | 1.60 |
| Laureth-4 | 1.60 |
| Glyceryl Monostearate/PEG 100 Stearate | 2.40 |
| Total | 100.00 |
| Propelant | 8.00 |
| RESULTS | |
| Foam quality | Good |

Note the composition can be reformulated with only a single agent and can likewise be reformulated with PEG or mixture of PEG instead of PG. Mixtures of PEG(s) and PG can also be used.

Example 21

Theoretical Propylene Glycol Based Composition with Two Active Agents

| Ingredients | 4B |
|---|---|
| Aluminum zirconium trichlorohydrex-glycine | 10.00 |
| Glycopyrrolate | 1.00 |
| Propylene glycol | 81.79 |
| Stearyl alcohol | 1.60 |
| Hydroxypropyl cellulose | 1.60 |
| Laureth-4 | 1.60 |
| Glyceryl Monostearate/PEG 100 Stearate | 2.40 |
| Total | 100.00 |
| Propellant | 8.00 |

Note the composition can be reformulated with only one active agent and can likewise be reformulated with PEG or mixture of PEG instead of PG. Mixtures of PEG(s) and PG can also be used. Glycopyrrolate may be applied at up to about 6%, preferably upto about 4% although at higher levels side effects may be observed. As will be appreciated the PG and or aluminum salt may be for example reduced by the amount the glycopyrrolate is increased.

What is claimed is:

1. A method of treating a disorder of the skin, a body cavity or mucosal surface, wherein the disorder involves excessive sweating as one of its symptoms, comprising:
   a) dispensing a foamable composition comprising a propellant and less than 5% short chain alcohols, having up to 5 carbon atoms in their carbon chain skeleton and one hydroxyl group, wherein the composition is stored in an aerosol container and upon dispensing the foamable composition forms a thermally stable breakable foam, the breakable foam composition comprising:
      i. an active agent, suitable for the treatment of hyperhidrosis;
      ii. about 2% to about 50% by weight of at least one carrier selected from the group consisting of a hydrophobic organic carrier, a solvent, an emollient and any mixture thereof;
      iii. about 0.1% to about 5% by weight of a surface-active agent;
      iv. about 0.01% to about 5% by weight of a polymeric agent selected from the group consisting of a bioadhesive agent, a gelling agent, a film forming agent and a phase change agent; and
      v. water,
   b) administering the resulting breakable foam topically to a subject having the disorder, wherein the foam does not collapse immediately upon exposure to skin temperature, and
   c) collapsing the breakable foam by applying shear force to the administered breakable foam such that it is spread at, about and within the target site;
   wherein the active agent is administered in a therapeutically effective amount; and
   wherein the composition has some or partial resistance to centrifugation at 3000 rpm for 10 minutes.

2. The method of claim 1, wherein
   the solvent is a polar solvent; and
   the administered breakable foam is absorbed.

3. The method of claim 1 or 2, wherein the composition further comprises about 0.1% to about 5% by weight of a foam adjuvant is selected from the group consisting of a fatty alcohol having 15 or more carbons in their carbon chain; a fatty acid having 16 or more carbons in their carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octocosanoic acid; 12-hydroxy stearic acid and any mixture thereof.

4. The method of claim 1, wherein the composition further comprises at least one component, selected from the group consisting of:
   i. co-emulsifier or foam stabilizer;
   ii. a viscosity, bulking or firming agent;
   iii. a stabilizer;
   iv. a foam adjuvant
   v. a co-solvent;
   vi. a penetration enhancer;
   vii. an agent capable of having an occlusive effect; and
   viii. a modulating agent.

5. The method of claim 1 wherein the propellant is itself a cooling agent.

6. The method of claim 1 wherein the foamed composition is flowable.

7. The method of claim 6, wherein the at least one carrier is selected from the group consisting of an oil, a silicone oil, an alcohol, a polyol, a polyethylene glycol (PEG), a propylene glycol, and a solvent, or combinations thereof.

8. The method of claim 6, wherein the sweating is reduced by at least 20% or about 20%.

9. The method of claim 6, wherein the composition further comprises a humectantat.

10. The method of claim 6, wherein the at least one carrier comprises a polar solvent.

11. The method of claim 1, wherein the foamed composition further comprises a co solvent at a concentration of about 0.1% to about 48% by weight of the total composition.

12. The method of claim 11, wherein the co solvent is at a concentration of about 0.1% to about 30% by weight of the total composition.

13. The method of claim 11, wherein the at least one carrier and the co-solvent are at a concentration of about 40% to about 90% by weight of the total composition.

14. The method of claim 1, wherein the foamed composition further comprises a second surface active agent.

15. The method of claim 1 wherein the polymeric agent is a combination of hydroxy propylmethyl cellulose and xantham gum.

16. The method of claim 1 wherein the polymeric agent is selected from the group consisting of sodium carboxymethyl-cellulose, hydroxyethyl-cellulose, microcrystalline-cellulose, aluminum starch octyl succinate, and polyacrylates; carbopol; hydroxy propylmethyl cellulose a hydroxypropyl-cellulose; and xantham gum.

17. The method of claim 1, wherein the foamed composition further comprises a co-emulsifier at a concentration of about 0.05% to about 10% by weight of the total composition.

18. The method of claim 1, wherein the foamed composition further comprises a viscosity, bulking or firming agent is a concentration of about 0.1% to about 15% by weight of the total composition.

19. The method of claim 1, wherein the foamed composition further comprises a stabilizer at a concentration of about 0.1% to about 10% by weight of the total composition.

20. The method of claim 1, wherein the foamed composition further comprises a penetration enhancer at a concentration of about 0.1% to about 30% by weight of the total composition.

21. The method of claim 1, wherein the foamed composition further comprises an agent capable of having an occlusive effect at a concentration of about 45% to about 85% by weight of the total composition.

22. The method of claim 1, wherein the foamed composition further comprises an agent capable of having an occlusive effect at a concentration of about 25% to about 49% by weight of the total composition.

23. The method of claim 1, wherein the foamed composition further comprises an agent capable of having an occlusive effect at a concentration of about 10% to about 30% by weight of the total composition.

24. The method of claim 1, wherein the foam has a density of about 0.01 to about 0.2 g/ml.

25. The method of claim 1, wherein the foam is a breakable foam, which if not subjected to mechanical shear break, is capable of having a collapse time of about 50 seconds or more.

26. The method of claim 1, wherein the foam is a breakable foam, which if not subjected to mechanical shear break, is capable of having a collapse time of about 120 seconds or more.

27. The method of claim 1, wherein the foam is a breakable foam, which if not subjected to mechanical shear break, is capable of having a collapse time of about 300 seconds or more.

28. The method of claim 1, wherein the foamed composition further comprises an aliphatic alcohol and a fatty alcohol.

29. The method of claim 1, wherein the foamed composition further comprises a foam adjuvant agent, selected from the group consisting of a fatty alcohol having 15 or more carbons in its carbon chain and a fatty acid having 16 or more carbons in its carbon chain.

30. The method of claim 1, wherein the carrier is a hydrophobic organic carrier selected from the group consisting of mineral oil, silicone oil, a triglyceride, an ester of a fatty acid, and petrolatum.

31. The method of claim 30, wherein the hydrophobic organic carrier is occlusive.

32. The method of claim 30, wherein the hydrophobic organic carrier is non occlusive.

33. The method of claim 1, wherein the foamed composition comprises up to 80% water.

34. The method of claim 1, wherein the foamed composition comprises less than 2% or about 2% short chain alcohols.

35. The method of claim 1, wherein the foamed composition is alcohol free.

36. The method of claim 1, wherein the foamed composition comprises an emulsion.

37. The method of claim 36, wherein the emulsion is selected from the group consisting of an oil in water emulsion; a water in oil emulsion; an oleaginous emulsion; a petrolatum in water emulsion; a water in petrolatum emulsion; a petrolatum in non aqueous solvent emulsion, a non aqueous solvent in petrolatum emulsion, a hydrophilic non aqueous solvent in petrolatum emulsion and a non aqueous emulsion.

38. The method of claim 1, wherein the foamed composition further comprises about 0.1% to about 5% by weight of a foam adjuvant selected from the group consisting of a fatty alcohol having 15 or more carbons in their carbon chain; a fatty acid having 16 or more carbons in their carbon chain; a fatty alcohol, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; cetyl alcohol; stearyl alcohol; arachidyl alcohol; behenyl alcohol; 1-triacontanol; hexadecanoic acid; stearic acid; arachidic acid; behenic acid; octacosanoic acid; 12-hydroxy stearic acid and any mixture thereof.

39. The method of claim 1, wherein the active agent is selected from the group consisting of:
a) An anticholinergic drug;
b) An agent, selected from the group consisting of boric acid, tannic acid, resorcinol, potassium permanganate, formaldehyde, glutaraldehyde and methenamine;
c) a Lewis acid;
d) a salt or a complex of a metal ion, capable of treating hyperhidrosis;
e) a salt or a complex of a metal ion selected from the group consisting of aluminum and zirconium;
f) a salt or a complex of a metal selected from the group consisting of aluminum and zirconium;
g) a 5-alpha-reductase inhibitor;
h) an agent, selected from the group consisting of finasteride, flutamide, spironolactone, saw palmetto extract, epristeride and cholestan-3-one;
i) an agent, capable of treating hyperhidrosis, selected from the group consisting of mono- and dicarboxylic acids having 4 to 18 carbon atoms, a mercapto derivative thereof, a salt thereof, and an ester thereof;
j) botulinum toxin;
k) a 5-HT2C receptor antagonist;
l) an agent, selected from the group consisting of ketanserin, ritanserin, mianserin, mesulergine, cyproheptadine, fluoxetine, mirtazapine, olanzapine, and ziprasidone;
m) a 5-HT2C receptor modulator; and
n) an antiperspirant.

40. The method of claim 1, wherein the foamed composition further comprises
at least one additional therapeutic agent selected from the group consisting of an anti-infective, an antibiotic, an antibacterial agent, an antifungal agent, an antiviral agent, an antiparasitic agent, a steroid, a non-steroidal antiinflammatory agent, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, an anti wrinkle agent, a skin whitening agent, a skin protective agent, a masking agent, an anti-wart agent, a refatting agent, a lubricating agent and any mixture thereof.

41. The method of claim 1, wherein the surface active agent includes a mixture of at least one non-ionic surfactant and at least one ionic surfactant in a ratio in the range of about 100:1 to 6:1.

42. The method of claim 1, wherein the surface active agent is non-ionic.

43. The method of claim 1, wherein the polymeric agent is selected from the group consisting of a water-soluble cellulose ether and a naturally-occurring polymeric material.

44. The method of claim 1, wherein the polymeric agent is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose, carboxymethylhydroxyethylcellulose, xanthan gum, guar gum, carrageenin gum, locust bean gum and tragacanth gum.

45. The method of claim 1 where the first agent is a hyperhidrosis agent and there is provided a second agent to treat another disorder, wherein the disorder is selected from the group consisting of a dermatose, a dermatitis, a vaginal disorder, a vulvar disorder, an anal disorder, a disorder of a body cavity, an ear disorder, a disorder of the nose, a disorder of the respiratory system, a bacterial infection, fungal infection, viral infection, dermatological pain, dermatological inflammation, acne, acne vulgaris, inflammatory acne, non-inflammatory acne, acne fulminans, nodular papulopustular acne, acne conglobata, dermatitis, bacterial skin infections, fungal skin infections, viral skin infections, parasitic skin infections, skin neoplasia, skin neoplasms, pruritis, cellulitis, acute lymphangitis, lymphadenitis, erysipelas, cutaneous abscesses, necrotizing subcutaneous infections, scalded skin syndrome, folliculitis, furuncles, hidradenitis suppurativa, carbuncles, paronychial infections, rashes, erythrasma, impetigo, ecthyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, grannuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, moles, Kaposi's sarcoma, melanoma, malignant melanoma, basal cell carcinoma, squamous cell carcinoma, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

* * * * *